United States Patent
Elmaanaoui et al.

(10) Patent No.: US 11,175,126 B2
(45) Date of Patent: Nov. 16, 2021

(54) AUTOMATED POLARIZATION CONTROL

(71) Applicant: Canon U.S.A., Inc., Melville, NY (US)

(72) Inventors: Badr Elmaanaoui, Belmont, MA (US);
Matthew Scott Pias, Brookline, MA (US); Pierre-Yves Mabboux, Arlington, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 16/823,164

(22) Filed: Mar. 18, 2020

(65) Prior Publication Data

US 2020/0318944 A1 Oct. 8, 2020

Related U.S. Application Data

(60) Provisional application No. 62/831,032, filed on Apr. 8, 2019.

(51) Int. Cl.
*G01B 9/02* (2006.01)
*A61B 3/10* (2006.01)

(52) U.S. Cl.
CPC ..... *G01B 9/02091* (2013.01); *G01B 9/02004* (2013.01); *G01B 9/02009* (2013.01);
(Continued)

(58) Field of Classification Search
CPC ............ G01B 9/02044; G01B 9/02068; G01B 9/02091; G01B 2290/45; G01B 2290/70
See application file for complete search history.

(56) References Cited

U.S. PATENT DOCUMENTS 5,202,745 A 4/1993 Sorin et al.
5,268,741 A 12/1993 Chou et al.
(Continued)

FOREIGN PATENT DOCUMENTS

EP 322893 A2 7/1989
JP 2007510143 A 4/2007
(Continued)

OTHER PUBLICATIONS

A.D. Kersey, et al., "Polarization diversity detection for fiber interferometers using active feedback control of output polarization-mode selection", Optics Letters, Optical Society of America, XP000162158, ISSN: 0146-9592, vol. 15, No. 22, Nov. 1990, pp. 1315-1317.
(Continued)

*Primary Examiner* — Michael A Lyons
(74) *Attorney, Agent, or Firm* — Canon U.S.A., Inc. I.P. Division

(57) ABSTRACT

One or more devices, systems, methods and storage mediums for optical imaging medical devices, such as, but not limited to, Optical Coherence Tomography (OCT), single mode OCT, and/or multi-modal OCT apparatuses and systems, and methods and storage mediums for use with same, for performing automated polarization control, polarization diversity and/or balanced detection are provided herein. One or more embodiments may achieve polarization diversity and balanced detection (or photo-detection) under any imaging circumstances. One or more embodiments, may achieve polarization control functionality regardless of whether such control is automatic or manual. Additionally, one or more embodiments may achieve automated polarization control, may achieve balanced detection (or photo-detection), and/or may address potential disturbances, such as, but not limited to, polarization drift over time, temperature and/or mechanical perturbations or variations. One or more embodiments may include an optical receiver where polarization diversity and balanced detection may be optimized via motorized controls.

21 Claims, 13 Drawing Sheets

(52) U.S. Cl.
CPC ..... *G01B 9/02041* (2013.01); *G01B 9/02044* (2013.01); *G01B 9/02068* (2013.01); *A61B 3/102* (2013.01); *G01B 2290/45* (2013.01); *G01B 2290/70* (2013.01)

(56) References Cited

U.S. PATENT DOCUMENTS

| | | | |
|---|---|---|---|
| 6,763,261 | B2 | 7/2004 | Casscells, III et al. |
| 7,366,376 | B2 | 4/2008 | Shishkov et al. |
| 7,742,173 | B2 | 6/2010 | Yun et al. |
| 7,843,572 | B2 | 11/2010 | Tearney et al. |
| 7,872,759 | B2 | 1/2011 | Tearney et al. |
| 7,889,348 | B2 | 2/2011 | Tearney et al. |
| 8,289,522 | B2 | 10/2012 | Tearney et al. |
| 8,676,013 | B2 | 3/2014 | Bouma et al. |
| 8,928,889 | B2 | 1/2015 | Tearney et al. |
| 9,086,264 | B2 | 7/2015 | Wang et al. |
| 9,087,368 | B2 | 7/2015 | Tearney et al. |
| 9,332,942 | B2 | 5/2016 | Jaffer et al. |
| 9,557,154 | B2 | 1/2017 | Tearney et al. |
| 9,995,565 | B2 | 6/2018 | Yamanari |
| 2006/0244973 | A1 | 11/2006 | Yun et al. |
| 2007/0278389 | A1 | 12/2007 | Ajgaonkar et al. |
| 2010/0092389 | A1 | 4/2010 | Jaffer |
| 2011/0292400 | A1 | 12/2011 | Fleming et al. |
| 2012/0101374 | A1 | 4/2012 | Tearney et al. |
| 2012/0224165 | A1* | 9/2012 | Swanson ............ G01B 9/02079 356/28.5 |
| 2014/0176960 | A1* | 6/2014 | Kemp .................. A61B 5/0066 356/479 |
| 2014/0276011 | A1 | 9/2014 | Schmitt et al. |
| 2016/0069664 | A1* | 3/2016 | Yamanari ........... G01B 9/02028 356/479 |
| 2016/0228097 | A1 | 8/2016 | Jaffer et al. |
| 2016/0231101 | A1 | 8/2016 | Swanson |
| 2017/0135584 | A1 | 5/2017 | Tearney et al. |
| 2017/0196459 | A1 | 7/2017 | Lam et al. |

FOREIGN PATENT DOCUMENTS

| | | |
|---|---|---|
| JP | 2009505073 A | 2/2009 |
| WO | 2016/015052 A1 | 1/2016 |
| WO | 2016/144878 A1 | 9/2016 |

OTHER PUBLICATIONS

Thorlabs.com website, "Balanced polarization diversity detector for PS-OCT", Internet Citation, XP002671014, May 2009, pp. 1-28, URL: htttp://www.thorlabs.com/Thorcat/19300/19384-D02.pdf [retrieved on Mar. 7, 2012].

Anthony M.D. Lee, et al., "Fiber-optic polarization diversity detection for rotary probe optical coherence tomography", Optics Letters, Optical Society of America, XP001589964, ISSN: 0146-9592, DOI; 10.1364/OL.39.003638, vol. 39, No. 12, Jun. 2014, pp. 3638-3641.

A.G. Podoleanu, "Unbalanced versus balanced operation in an optical coherence tomography system", Applied Optics, vol. 39, Issue No. 1, Jan. 2000, 173-182.

W. Drexler, et al., "Optical Coherence Tomography: Technology and Applications", 2nd edition, vol. 1, Springer Reference, Chapters 7, 33, and 70, Sep. 2015, pp. 225-254, 1055-1101, and 2131-2152 (including title page and copyright page).

Thorlabs.com website, "In-Line Fiber Optic Polarization Controllers", screenshots obtained at https://www.thorlabs.com/newgrouppage9.cfm?objectgroup_ID=2161 on Mar. 16, 2020 (previously viewed on Mar. 8, 2020), six pages.

* cited by examiner

Results: Polarization error as a function of polarization controllers

AUTOMATED POLARIZATION CONTROL

CROSS-REFERENCE TO RELATED APPLICATION(S)

This application relates, and claims priority, to U.S. Patent Application Ser. No. 62/831,032, filed Apr. 8, 2019, the entire disclosure of which is incorporated by reference herein in its entirety

FIELD OF THE DISCLOSURE

The present disclosure relates generally to the field of medical imaging and processing medical image data, and more particularly to apparatuses, systems, and methods and storage mediums for use therewith, that perform automated polarization control, polarization diversity and/or balanced detection.

BACKGROUND OF THE DISCLOSURE

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

Optical receivers may be used for optical fiber reflectometry techniques, such as Optical Coherence Domain Reflectometry (OCDR) and Optical Fourier-Domain Reflectometry (OFDR). Optical receivers are interferometric in nature where two electromagnetic waves, usually linearly polarized, generate an interference pattern. Typically, the optical fibers used in optical fiber reflectometry are single-mode (SM) fibers that do not maintain polarization. One can therefore potentially end up with a situation where the two electromagnetic waves are polarized 90 degrees from or of each other, which would, therefore, not produce any interference pattern. More often, one ends up with a situation where the two electromagnetic waves do interfere but not efficiently because the polarizations are mis-aligned. In such a case, some of the interfering signal is lost.

Polarization diverse optical receivers have been used to address any lack of interference pattern generation or to address inefficient interference as aforementioned. The principle is to split the two electromagnetic waves, numbered, for example, 1 and 2, along two controlled polarization axes, labeled, for example, x and y. In such an example, one ends up with a total of 4 electromagnetic waves x1, y1, x2 and y2. Out of those waves, two interfering patterns are produced from the interfering of x1 and x2 waves along the x axis on one hand and y1 and y2 along the y axis on the other hand. Two photodetectors are used to capture those two interfering signals.

Following initial applications in optical fiber reflectometry, polarization diverse optical receivers were later used in Optical Coherence Tomography (OCT), for example, in cardiovascular OCT where polarization non-maintaining single-mode optical fibers are also used to carry the optical signal in and out of the body. Polarization diverse optical receivers may also be implemented in ophthalmologic OCT, but may have less significance because the electromagnetic waves there typically propagate in free space (polarization is maintained in this example). However, an issue arises in a lack of clarity regarding how to best select polarization axes or achieve polarization diversity.

Another issue arises in providing optical receivers with balanced detection. For example, balanced detection (or balanced photo-detection) may be important to have in one or more OCT systems because an optical signal gathered from a sample may be very weak and a signal-to-noise ratio (SNR) may be a useful benchmark. However, a lack of clarity exists regarding how to best achieve balanced detection.

In particular, it remains unclear on how to set up an optical receiver that achieves both polarization diversity (e.g., where a best choice is made for selecting the polarization axes, such as an x and y axis) and balanced detection (or photo-detection) (e.g., where there is a proper 50%/50% light split before sending such light to a detector or detectors).

In the past, polarization diversity has been controlled manually, and there has been no automation to adjust the polarization.

Previous optical receivers, and controllers for same, also fail to address any potential disturbances, such as, but not limited to, polarization drift over time, temperature and/or mechanical perturbations or variations.

Accordingly, it would be desirable to provide at least one imaging (e.g., OCT, etc.) technique (and/or at least one feature or option), storage medium and/or apparatus or system for use in at least one optical device, assembly or system to achieve polarization diversity and balanced detection (or photo-detection), especially in a way that reduces or minimizes cost of manufacture and maintenance. There is also a need to achieve automated polarization control, and a need exists to address potential disturbances, such as, but not limited to, polarization drift over time, temperature and/or mechanical perturbations or variations.

SUMMARY

Accordingly, it is a broad object of the present disclosure to provide imaging (e.g., OCT (for example, but not limited to, using an interference optical system, such as an interferometer (e.g., spectral domain OCT (SD-OCT), Swept Source OCT (SS-OCT), etc.)), etc.) apparatuses and systems that operate to select an appropriate method and/or perform automatic polarization control and/or balanced detection, and methods and storage mediums for use with same.

One or more embodiments may achieve polarization diversity and balanced detection (or photo-detection) under any imaging circumstances. One or more embodiments, may achieve polarization control functionality regardless of whether such control is automatic or manual. Additionally, one or more embodiments may achieve automated polarization control, may achieve balanced detection (or photodetection), and/or may address potential disturbances, such as, but not limited to, polarization drift over time, temperature and/or mechanical perturbations or variations.

One or more embodiments include an optical receiver where polarization diversity and balanced detection may be optimized via motorized controls. Such embodiments offer a way to automatically adjust the optical receiver so that interfering signals are improved or maximized. Optimization increases the signal-to-noise ratio (SNR) and improves the overall image quality.

One or more embodiments control polarization such that the polarization does not change, or does not substantially change (e.g., the polarization stays about the same or stays approximately constant), in response to the one or more potential disturbances, such as, but not limited to, polarization drift over time, temperature and/or mechanical perturbations or variations.

One or more embodiments provides constant polarization control even in cases where vibration and/or a bending of one or more optical fibers occurs, especially where the optical fiber(s) travel(s) into a body of a patient and go through sharp bend(s) to access one or more predetermined areas of the patient (such as, but not limited to, one or more cardiovascular arteries, one or more eye areas (in ophthalmology applications), etc.).

One or more embodiments may use one or more polarization controllers to achieve polarization diversity, balanced detection, and/or control polarization. One or more embodiments may use hybrid polarization controllers, with both manual adjustment and motor control. One or more embodiments may reduce or minimize a polarization error signal by a predetermined or certain amount or quantity, and may drive an overall polarization control scheme using the predetermined or certain amount or quantity. One or more embodiments may generate the polarization error signal via a dedicated electronic module or circuitry. Additionally or alternatively, one or more embodiments may use raw outputs of the balanced photo-detector or detector(s), and/or may use a three output (3-output) balanced photodetector or detectors. Additionally or alternatively, one or more embodiments may use a digital signal or a digitizer having four channels that operates to receive and process received signals (e.g., four signals; four signals where each signal of the four signals is received via one respective channel of the four channels of the digitizer; etc.) to determine the reduced or minimized polarization control error signal and to output the polarization control error signal.

In one or more embodiments, a polarization error signal (e.g., in a case where the polarization error signal or polarization control error signal is generated and output using an analog signal (e.g., converted via an Analog-to-Digital converter) or an analog converter or processing module) may be low-pass filtered to provide several advantages, such as, but not limited to, no need for high speed data acquisition, no need to synchronize the micro-controller, does not burden a main OCT data acquisition board (OCT DAQ), polarization control is completely decoupled from the main OCT DAQ, etc. One or more embodiments may use a generic micro-controller to read the polarization error signal and act upon the motorized polarization controllers. Micro-controller firmware may be programmed to reduce and/or minimize the error signal (e.g., having a design of a control loop). The polarization control procedure may achieve greater processing speed and accuracy in view of the method(s) and structure(s) discussed herein. In one or more embodiments, the micro-controller may also monitor the error signal in real time, and may alert and correct any polarization issues. This ensures that any one or more embodiments of a OCT device, apparatus, system, method or storage medium discussed herein continue to operate at peak performance. In one or more embodiments, the polarization control unit may not use, or does not need to use, the OCT DAQ.

One or more embodiments achieving balanced photodetection operate to provide common noise rejection and greatly reduce a relative intensity noise (RIN) produced by a light or laser source. One or more embodiments achieve detection balance by splitting light (e.g., from a light source) 50/50 or 50%/50% and feeding the split signals to a balanced photodetector or detectors (BPD). Balanced detection may be achieved in one or more embodiments where there is a proper 50%/50%, or approximately 50/50 or 50%/50%, light split before sending such light to a detector or detectors.

One or more embodiments may provide or include polarization diverse balanced optical receivers in one or more applications, such as, but not limited to, OCT applications.

One or more embodiments may optimally or ideally select polarization axes to provide a polarization diverse optical receiver(s). In one or more of such embodiments, a polarization diverse optical receiver may operate to maintain polarization, including in situations where the optical fibers used are single mode (SM) fibers, and/or may operate to achieve efficient one or more interference patterns from at least two electromagnetic waves. One or more embodiments operate such that polarization axes (e.g., where a best choice is made for selecting the polarization axes, such as an x axis and a y axis, etc.) are chosen carefully and optimally so as to improve or maximize interferences on both axes.

It is also a broad object of the present disclosure to provide imaging apparatuses, systems, methods and storage mediums to the field of minimally invasive medical imaging devices, including, but not limited to, optical coherence tomography (OCT). One or more embodiments of the present disclosure enable providing one or more automatic polarization control features for any cases or procedures. More generally stated, by using the configuration(s) and function(s)/option(s)/technique(s) discussed herein, polarization control (including automatic polarization control) feature(s), balanced detection feature(s), and/or polarization diverse balanced detection (or photo-detection) feature(s) may be provided.

In accordance with one or more embodiments of the present disclosure, imaging (e.g., OCT, IVUS, etc.) apparatuses and systems, and methods and storage mediums may operate to characterize tissue type in addition to providing a morphological image to help an operator's diagnostic decision based on quantitative tissue information. In accordance with one or more embodiments of the present disclosure, imaging (e.g., OCT, etc.) apparatuses and systems, and methods and storage mediums may operate to characterize biological objects other than tissue. For example, the characterization may be of a biological fluid such as blood or mucus (e.g., using OCT, such as, but not limited to, multi-modality optical coherence tomography (MM-OCT), single mode (SM) OCT, swept source OCT (SS-OCT), polarization sensitive OCT (PS-OCT), etc.).

One embodiment of the present disclosure is directed to at least one processor selecting an appropriate option for achieving/performing one or more of: automatic polarization control, balanced detection, and/or polarization diversity.

At least one embodiment of the present disclosure is directed to a method for generating and/or displaying an anatomical image on a graphical user interface. The method may initiate with acquiring an anatomical image or multiple anatomical images of a predetermined target of a patient (e.g., a coronary artery, a blood vessel, an eye, etc.) and acquiring a plurality of intravascular image frames of the predetermined target of the patient associated with the anatomical image at a plurality of acquisition locations.

In one or more embodiments of the present disclosure, it is possible to, in imaging (e.g., OCT, etc.), reduce the size of the optical apparatus and/or system and acquire black and white and/or color images. That said, in one or more embodiments, size reduction may not be an issue in a case where it is possible to specify a location of the pullback (e.g., OCT pullback, etc.) in an image, such as, but not limited to, an angiography image.

In one or more embodiments, a target area (e.g., a blood vessel, a coronary artery, an eye, etc.) may flushed with a flushing media or agent and/or a contrast agent (in one or more embodiments, the flushing media or agent may include or encompass a contrast agent), and then pullback of the imaging probe or catheter is performed to acquire the one or more images.

According to other aspects of the present disclosure, one or more additional apparatuses, one or more systems, one or more methods, and one or more storage mediums using automatic polarization control and/or features/functions/techniques to select an appropriate polarization diversity and/or balanced detection method and/or structural arrangement based on available imaging condition(s), such as, but not limited to, angiography image condition(s), are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE EMBODIMENTS

Figure 1:
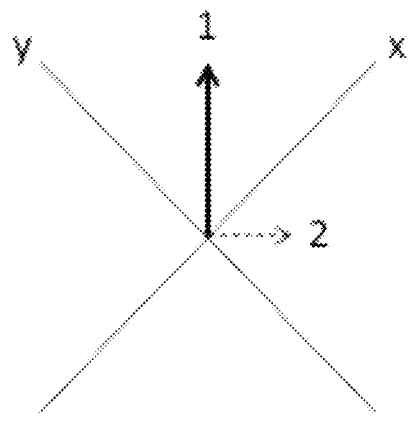
FIG. 1 is a diagram example of two non-interfering electromagnetic waves that is addressed by one or more embodiments discussed herein in accordance with one or more aspects of the present disclosure.

Embodiments will be described below with reference to the attached drawings. Like numbers refer to like elements throughout. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an endoscope as disclosed in the following which is used to inspect an inside a human body may also be used to inspect other objects. Examples of specialized endoscopes which are examples of endoscope in which an embodiment may be implemented including: angioscope; anoscope; arthroscope; arterioscope; bronchoscope; capsule endoscope; choledochoscope; colonoscope; colposcope; cystoscope; encephaloscope; esophagogastroduodenoscope; esophagoscope; gastroscope; hysteroscope; laparoscope; laryngoscope; mediastinoscope; nephroscope; neuroendoscope; proctoscope; resectoscope; rhinoscope; sigmoidoscope; sinusoscope; thoracoscope; ureteroscope; uteroscope; borescope; fiberscope; inspection camera; and any specialized endoscope which may be adapted to include an embodiment. The endoscope may be flexible or rigid. An embodiment may also be a probe or an imaging apparatus.

One or more devices, optical systems, methods, and storage mediums for obtaining a direct image (e.g., black and white, color, etc.) of a subject, such as tissue or an object, using an imaging function, feature, technique or method (e.g., OCT (for example, but not limited to, using an interference optical system, such as an interferometer (e.g., spectral domain OCT (SD-OCT), Swept Source OCT (SS-OCT), etc.)), etc.); and for using and/or performing automatic polarization control, polarization diversity and/or balanced detection, and methods and storage mediums for use with same while utilizing, improving or maximizing an imaging feature, function or technique are disclosed herein. In accordance with at least one aspect of the present disclosure, one or more devices, optical systems, methods, and storage mediums discussed herein use an imaging function, feature, technique or method; an automatic polarization control, polarization diversity and/or balanced detection function, feature, technique or method; and/or selecting an appropriate automatic polarization control, polarization diversity and/or balanced detection method for use in an apparatus or system.

One or more embodiments may achieve polarization diversity and balanced detection (or photo-detection) under any imaging circumstances. One or more embodiments, may achieve polarization control functionality regardless of whether such control is automatic or manual. Additionally, one or more embodiments may achieve automated polarization control, may achieve balanced detection (or photo-detection), and/or may address potential disturbances, such as, but not limited to, polarization drift over time, temperature and/or mechanical perturbations or variations. One or more embodiments discussed herein addresses single-mode fiber sensitivity to temperature variation, and addresses polarization changes based on vibration and/or the bending of optical fiber(s). Preferably where optical fiber(s) travel(s) into an object or subject (e.g., a body of a patient) and has to go through sharp bends to access a target area (e.g., one or more cardiovascular arteries), embodiments also address mechanical variation due to such fiber condition(s) and changes.

Figure 2:
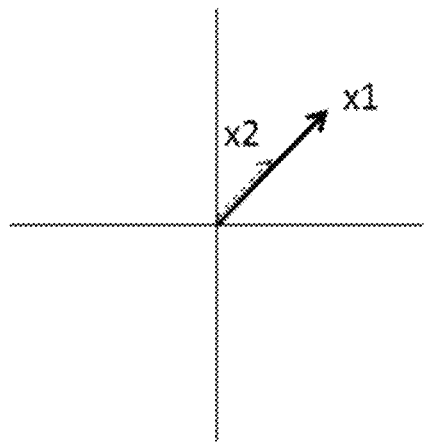
FIGS. 2-3 show examples of aligned electromagnetic waves after splitting that will create respective interference patterns that may be used in one or more embodiments discussed herein in accordance with one or more aspects of the present disclosure.
Figure 3:
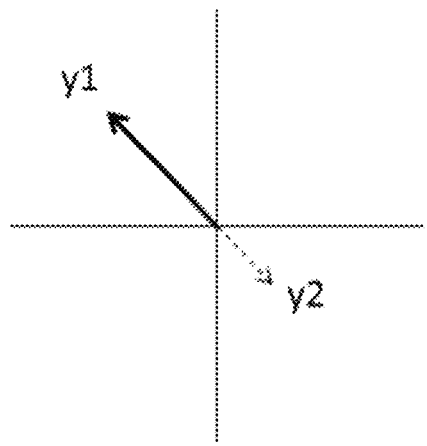

Turning now to the details of the figures, FIG. 1 shows a situation having two non-interfering electromagnetic waves, where the linear polarization is 90 deg of each other. The axis 'x' and 'y' are the proposed polarization axis to create waves x1, y1, x2 and y2. When viewed together, FIGS. 2-3 show all four (4) electromagnetic waves of this example after splitting. In FIG. 2, waves x1 and x2 are aligned along the 'x' axis (in other words, waves x1 and x2 are polarized along the 'x' axis), and operate to create an interference pattern. In FIG. 3, waves y1 and y2 are aligned along the 'y' axis (in other words, waves y1 and y2 are polarized along the 'y' axis), and operate to create an interference pattern.

Preferably, in one or more embodiments, the polarization axes (x, y) are not random, and are preferably chosen carefully so as to improve or maximize interferences on both axes. Preferably, the polarization axis is chosen so that each wave 1 and 2 is split into two non-zero signals. The axis preferably should not coincide with the original directions of waves '1' and '2' as this leads to having one component be zero (x1=0 or y1=0 or x2=0 or y2=0). In other terms, preferably axis 'x' and axis 'y' are chosen so as to stay away from the polarization directions of waves '1' and '2'. In the embodiment example of FIGS. 2-3, the 'x' and 'y' axes were chosen such that x1=y1 and x2=y2, meaning that light is split evenly between the two polarization axes. This may be considered the ideal case for one or more embodiments to achieve polarization diversity.

One or more embodiments include an optical receiver where polarization diversity and balanced detection may be optimized via motorized controls. Such embodiments offer a way to automatically adjust the optical receiver so that interfering signals are improved or maximized. Optimization increases the signal-to-noise ratio (SNR) and improves the overall image quality.

One or more embodiments control polarization such that the polarization does not change, or does not substantially change (e.g., the polarization stays about the same or stays approximately constant), in response to the one or more potential disturbances, such as, but not limited to, polarization drift over time, temperature and/or mechanical perturbations or variations.

One or more embodiments provides constant polarization control even in cases where vibration and/or a bending of one or more optical fibers occurs, especially where the optical fiber(s) travel(s) into a body of a patient and go through sharp bend(s) to access one or more predetermined areas of the patient (such as, but not limited to, one or more cardiovascular arteries, one or more eye areas (in ophthalmology applications), etc.).

Figure 4:
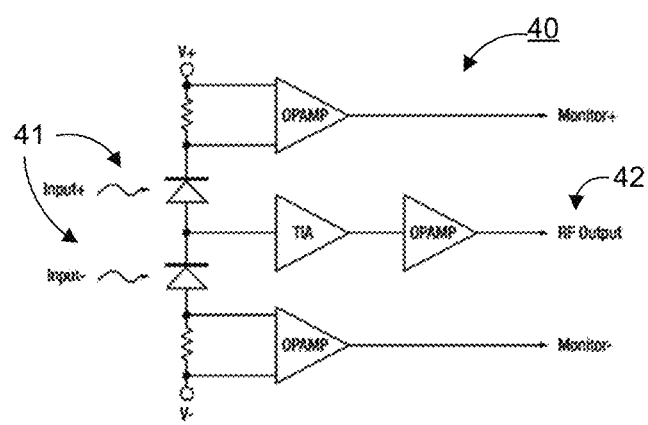
FIG. 4 shows at least one embodiment example of a balanced detector (or photodetector) that may be used in one or more embodiments discussed herein in accordance with one or more aspects of the present disclosure.

One or more embodiments achieving balanced photo-detection operate to provide common noise rejection and greatly reduce a relative intensity noise (RIN) produced by a light or laser source. One or more embodiments achieve detection balance by splitting light (e.g., from a light source) 50/50 or 50%/50% and feeding the split signals to a balanced photodetector or detectors (BPD). Balanced detection may be achieved in one or more embodiments where there is a proper 50%/50%, or approximately 50/50 or 50%/50%, light split before sending such light to a detector or detectors. FIG. 4 shows at least one embodiment example of a balanced detector (or photodetector) 40 that may be used in one or more embodiments. For example, as shown in FIG. 4, the balanced detector (or photodetector) 40 includes two (2) optical inputs 41 and one electrical output 42 where each photo-detector detects an interfering pattern of an optical signal. One or more embodiments may monitor electrical signals as an optional feature. Preferably, to maximize balanced detection and achieve greatest efficiency, the optical signal is split and fed to the balanced photodetector with a 50/50 ratio as aforementioned. While one or more embodiments may deviate from the 50/50 ratio, one or more other embodiments preferably include the 50/50 ratio, or a ratio that is substantially the same as the 50/50 ratio, to reduce or minimize noise and increase or maximize performance of the device, apparatus, system or storage medium using balanced detection. In one or more embodiments, the balance may be achieved by splitting the light from the light source approximately 50/50 or 50%/50%, and in one or more embodiments approximately 50/50 or 50%/50% may be one or more of the following: 40%/60%, about 40%/60%, 45%/55%, about 45%/55%, 55%/45%, 50%/50%, about 50%/about 50%, about 55%/45%, 60%/40%, about 60%/40% and/or a percentage that is within or equal to 10% from 50% (e.g., any value from about 40% to about 60%, any value from about 60% to about 40%, etc.)/another percentage that is within or equal to 10% from 50% (e.g., any value from about 40% to about 60%, any value from about 60% to about 40%, etc.). Any reference herein to 50%/50%, 50/50, about 50/50, or about 50%/50% encompasses such embodiments. For example, a reference to a 50/50 PBS or a 50/50 splitter herein may include or be comprised of a 40%/60% or a 60%/40% splitter. In one or more embodiments, the percentage/percentage light split is predetermined or selected to achieve a desired balanced detection and a desired polarization diversity (e.g., a 50%/50% split may be more optimal than a 45%/55% split, or other ratio for the split, depending on the circumstances, but a user may still desire and find acceptable a 45%/55% split to achieve an improved image quality). Indeed, all of the ratios discussed herein may be used in one or more embodiments, and alternative embodiments may further modify the light split ratio depending on a desired condition(s) or specification(s) for a device, apparatus, or system.

One or more embodiments may provide or include polarization diverse balanced optical receivers in one or more applications, such as, but not limited to, OCT applications. Indeed, one or more optical receiver embodiments discussed herein combines both polarization diversity and balanced detection or (photo-detection). Variations for such optical receivers may be implemented depending on whether the OCT device or system is free-space based (e.g., for ophthalmology applications) or optical fiber-based (e.g., for cardiovascular applications). One or more embodiments of the instant disclosure also may combine both single-mode (SM) fibers (which may not operate to maintain polarization) with polarization-maintaining fibers.

One or more embodiments may optimally or ideally select polarization axes, as aforementioned, to provide a polarization diverse optical receiver(s). In one or more of such embodiments, a polarization diverse optical receiver may operate to maintain polarization, including in situations where the optical fibers used are single mode (SM) fibers, and may operate to achieve efficient one or more interference patterns from at least two electromagnetic waves. One or more embodiments operate such that polarization axes (e.g., where a best choice is made for selecting the polarization axes, such as an x axis and a y axis, etc.) are chosen carefully and optimally so as to improve or maximize interferences on both axes.

Figure 5A:
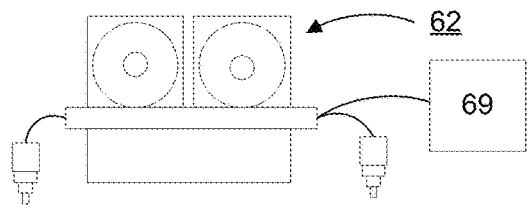
FIGS. 5A-5B show embodiment examples of a 2-paddle polarization controller and a 3-paddle polarization controller, respectively, that may be used in one or more embodiments discussed herein in accordance with one or more aspects of the present disclosure.
Figure 5B:
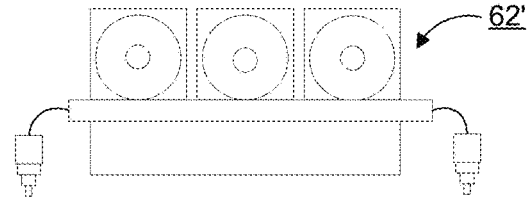

One or more embodiments may use one or more polarization controllers to achieve polarization diversity, balanced detection, and/or control polarization. One or more embodiments may use hybrid polarization controllers, with both manual adjustment and motor control. One or more embodiments may reduce or minimize a polarization error signal by a predetermined or certain amount or quantity, and may drive an overall polarization control scheme using the predetermined or certain amount or quantity. One or more embodiments may generate the polarization error signal via a dedicated electronic module or circuitry. Additionally or alternatively, one or more embodiments may use raw outputs of the balanced photo-detector or detector(s), and/or may use a three output (3-output) balanced photodetector or detectors. FIGS. 5A-5B show embodiment examples of a 2-paddle polarization controller 62 and a 3-paddle polarization controller 62', respectively, that may be used in one or more embodiments. Rotating the paddles creates stress in a fiber changing the optical polarization. Such paddle-type polarization controllers 62, 62' may have different numbers of paddles (e.g., two paddles in FIG. 5A, three paddles in FIG. 5B, etc.). Depending on the design (number of paddles, number of times the fiber is looped around the paddle, etc.), a user may vary polarization accuracy and range depending on desired settings for a given or predetermined situation or case.

In one or more embodiments, a polarization error signal may be low-pass filtered to provide several advantages, such as, but not limited to, no need for high speed data acquisition, no need to synchronize the micro-controller, does not burden a main OCT data acquisition board (OCT DAQ), polarization control is completely decoupled from the main OCT DAQ, etc. One or more embodiments may use a generic micro-controller to read the polarization error signal and act upon the motorized polarization controllers. Micro-controller firmware may be programmed to reduce and/or minimize the error signal (e.g., having a design of a control loop). The polarization control procedure may achieve greater processing speed and accuracy in view of the method(s) and structure(s) discussed herein. In one or more embodiments, the micro-controller may also monitor the error signal in real time, and may alert and correct any polarization issues. This ensures that any one or more embodiments of a OCT device, apparatus, system, method or storage medium discussed herein continue to operate at peak performance.

It is also a broad object of the present disclosure to provide imaging apparatuses, systems, methods and storage mediums to the field of minimally invasive medical imaging devices, including, but not limited to, optical coherence tomography (OCT). One or more embodiments of the present disclosure enable providing one or more automatic polarization control, one or more balanced detection and/or one or more polarization diversity features for any cases or procedures. More generally stated, by using the configuration(s) and function(s)/option(s)/technique(s) discussed herein, polarization control (including automatic polarization control) feature(s), balanced detection feature(s), and/or polarization diverse balanced detection (or photo-detection) feature(s) may be provided.

In accordance with one or more embodiments of the present disclosure, imaging (e.g., OCT, etc.) apparatuses and systems, and methods and storage mediums may operate to characterize tissue type in addition to providing a morphological image to help an operator's diagnostic decision based on quantitative tissue information. In accordance with one or more embodiments of the present disclosure, imaging (e.g., OCT, etc.) apparatuses and systems, and methods and storage mediums may operate to characterize biological objects other than tissue. For example, the characterization may be of a biological fluid such as blood or mucus (e.g., using OCT, such as, but not limited to, multimodality optical coherence tomography (MM-OCT), single mode (SM) OCT, swept source OCT (SS-OCT), polarization sensitive OCT (PS-OCT), etc.).

One embodiment of the present disclosure is directed to at least one processor selecting an appropriate option for achieving/performing one or more of: automatic polarization control, balanced detection, and/or polarization diversity.

At least one embodiment of the present disclosure is directed to a method for generating and/or displaying an anatomical image on a graphical user interface. The method may initiate with acquiring an anatomical image or multiple anatomical images of a predetermined target of a patient (e.g., a coronary artery, a blood vessel, an eye, etc.) and acquiring a plurality of intravascular image frames of the predetermined target of the patient associated with the anatomical image at a plurality of acquisition locations.

In one or more embodiments of the present disclosure, it is possible to, in imaging (e.g., OCT, etc.), reduce the size of the optical apparatus and/or system and acquire black and white and/or color images. That said, in one or more embodiments, size reduction may not be an issue in a case where it is possible to specify a location of the pullback (e.g., OCT pullback, etc.) in an image, such as, but not limited to, an angiography image.

In one or more embodiments, a target area (e.g., a blood vessel, a coronary artery, an eye, etc.) may flushed with a flushing media or agent and/or a contrast agent (in one or more embodiments, the flushing media or agent may include or encompass a contrast agent), and then pullback of the imaging probe or catheter is performed to acquire the one or more images.

Figure 6:
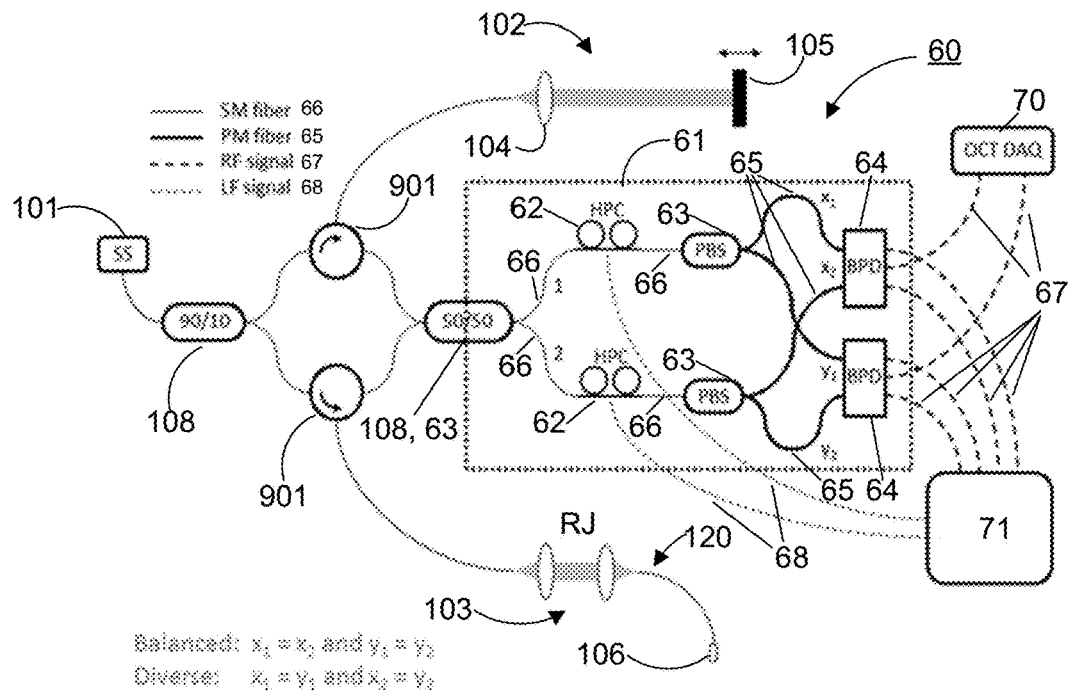
FIG. 6 is at least one embodiment example utilizing automated polarization control, balanced detection and/or polarization diversity in accordance with one or more aspects of the present disclosure.

One or more embodiments of the present disclosure that provide one or more automatic polarization control, one or more balanced detection and/or one or more polarization diversity features for any cases or procedures may be achieved by several different configurations discussed herein. By way of at least one embodiment example, FIG. 6 shows at least one embodiment of a motorized polarization-diverse balanced optical receiver 61 where a light source (e.g., light source 101) is a swept laser source (SS). Preferably, the laser signal is split (e.g., via a deflected or deflecting section 108, via a circulator 901, via any other splitter or deflecting element, via any splitter or deflected or deflecting element/section discussed herein, etc.) where 90% of the laser intensity goes towards a sample arm (e.g., a sample arm 103, a sample arm 103 including a probe or catheter (e.g., such as a probe or catheter 120), etc.) and 10% goes towards a reference arm (e.g., a reference arm 102) of the imaging device, apparatus or system (see e.g., device or system 60 of FIG. 6, device or system 100 discussed below, device or system 100' discussed below, device or system 100" discussed below, any other device or system discussed herein, etc.), such as, but not limited to, for OCT applications. In one or more embodiments, the balance may be achieved by splitting the light or laser signal approximately 90/10 or 90%/10%, and in one or more embodiments approximately 90/10 or 90%/10% may be one or more of the following: 99%/1%, about 100%/about 0%, 85%/15%, about 85%/15%, 95%/5%, about 95%/about 5%, 90%/10%, about 90%/about 10%, 80%/20%, about 80%/about 20%, and/or a percentage that is within or equal to 10% from 90% (e.g., any value from about 80% to about 100%, about 85% to about 95%, etc.)/another percentage that is within or equal to 20% from 0% (e.g., any value from about 0% to about 20%, any value from about 0% to about 10%, any value from about 0% to about 15%, etc.). Any reference herein to 90%/10%, 90/10, about 90/10, or about 90%/10% encompasses such embodiments. Each optical path may then travel through dedicated 3-way circulators, such as, but not limited to, the circulator 901 as discussed below, (e.g., which operate to pass light from the light source (e.g., the light source 101) to the reference arm (e.g., the reference arm 102) and from the reference arm (e.g., the reference arm 102) to the optical receiver 61 and which operate to pass light from the light source (e.g., the light source 101) to the sample arm (e.g., the sample arm 103) and from the sample arm (e.g., the sample arm 103) (e.g., after interaction with a sample, a target (e.g., the target 106 discussed below), object, etc.) to the optical receiver 61, respectively, etc.). The reference arm (e.g., the reference arm 102) may be made of a motorized delay line (MDL) which operates to adjust the optical path length (preferably both reference and sample arms 102, 103, respectively, have the exact same path length to get interference in one or more embodiments, for example). FIG. 6 shows graphically that the light travels out of the optical fiber into free space, is collimated by a lens 104, travels to a moving mirror (e.g., a reference mirror or reference reflection/reflector 105 discussed herein) and back into the optical fiber along the reference arm (e.g., the reference arm 102). In a same or similar manner, the light in the sample arm (e.g., the sample arm 103) may go through a rotary junction (e.g., a free-space section, rotary junction RJ as discussed herein, etc.), which enables light to transfer from a static optical fiber to another fast rotating fiber. The light may then travel to a distal end of a catheter (see e.g., the catheter or probe 120 discussed below) where the light is delivered to the target (e.g., the target 106), object, or subject (e.g., vascular tissue) to image. A portion of the light is reflected and/or back-scattered by the target (e.g., the target 106), object, or subject (e.g., the vascular tissue).

As both optical signals travel back from the reference arm (e.g., the reference arm 102) and sample arm (e.g., the sample arm 103), the optical signals may go through the aforementioned 3-way circulators 901 and are combined. The optical receiver 61 starts at this point where the newly-combined signal is split by a predetermined ratio (e.g., a 50/50 ratio as aforementioned; about, substantially or approximately 50/50 ratio; etc.) as signals 1 and 2. The optical signals may then go through polarization controls.

The present disclosure uses the term HPC for hybrid polarization controllers 62. The HPC term signifies that those polarization controllers may be controlled manually and/or via a motor. For example, one can have an assembly made of two polarization controllers (see e.g., the polarization controller 62 of FIG. 5A, the polarization controller 62' of FIG. 5B, etc.), one manual and the other one motorized (see e.g., motor 69 of FIG. 5A, which operates to automate polarization control). The polarization controllers 62 determine how the optical signals may be split by polarizing beam splitters (PBS) 63 shown, for example, in FIG. 6. After the PBSs 63 split up the optical signals, a result of having four (4) optical signals, for example, x1, x2, y1 and y2, is achieved, and the four optical signals may be sent to two (2) balanced photo-detectors (BPD) 64, for example, as shown in FIG. 6. In one or more embodiments, it is preferably that Polarization-maintaining optical fibers (PM-fibers) 65 are used between the PBSs 63 and the BPDs 64. While one or more embodiments may have variations, preferably, the four (4) optical PM-fibers 65 have equivalent or substantially equivalent lengths.

Regarding the BPDs 64, one or more embodiments may use any balanced output, and also may use two raw monitor outputs. As such, one or more embodiments preferably use a 3-output BPD 64 for each of the BPD's (e.g., as shown in FIG. 6). The main balanced output may go to an OCT Data Acquisition board (OCT DAQ 70) to collect the OCT data. The raw monitor outputs preferably are used as inputs to the polarization control unit (PCU) 71 (also referred to herein as a polarization control processor (PCP)). The PCU 71 preferably uses those values as feedback to control one or more of the HPCs 62. At least one objective of the PCU 71, in one or more embodiments, is to achieve optimal polarization-diversity and balanced detection. As explained above, balanced detection may be achieved when x1=x2 and y1=y2 (also referred to herein and/or in the figures with subscripts, such as, but not limited to $x_1$, $x_2$, $y_1$, $y_2$, etc. For example, unless otherwise specified, x1 and $x_1$ may be used interchangeably). In one or more embodiments, optimal or efficient polarization-diversity has x1=y1 and x2=y2. In one or more additional embodiments, an output fiber of the PBSs 63 may be PM-fiber 65 mated to SM fiber (66)-terminated photodiodes. In one or more further embodiments, the PBSs 63 may be connected to the BPDs 64 using all SM fibers 66.

While one or more embodiments may include similar or the same features as the embodiment shown in FIG. 6, one or more other embodiments may include variations (see e.g., at least FIGS. 7-12 discussed further below). For example, as shown in one or more of FIGS. 7-12, one of the polarization controllers 62 may be moved to various alternate locations on the reference arm side of the interferometer. All of the subject alternate designs preferably make use of two (2) polarization controllers 62, as done the same or similarly to the embodiment of FIG. 6. Preferably, the HPCs 62 are electrically connected to the polarization control unit (PCU) 71. That said, in one or more alternative embodiments, only one (1) polarization controller 62 may be used; in one or more of such alternative embodiments, a section of the optical receiver (e.g., the optical receiver 60, the optical receiver 60', any other optical receiver discussed herein, etc.) may no longer be fiber-based and may make use of free-space optics. In one or more embodiments, a 50/50 splitter (e.g., a deflecting or deflected section 108, a 50/50 PBS 63, etc.) or PBS 63 at a detection arm (e.g., at the PCU 71, in the optical receiver (e.g., the optical receiver 60, the optical receiver 60', any other optical receiver discussed herein, etc.), before the optical receiver (e.g., the optical receiver 60, the optical receiver 60', any other optical receiver discussed herein, etc.), before the PCU 71, etc.) may make use of PM-fibers 65 between the splitter (e.g., a deflecting or deflected section 108, a 50/50 PBS 63, etc.) and one or more PBSs 63. For example, in one or more embodiments, the output of the splitter (e.g., a deflecting or deflected section 108, a 50/50 PBS 63, etc.) may be a PM-fiber 65 and the input of the PBSs 63 may be a PM-fiber 65.

Figure 7:
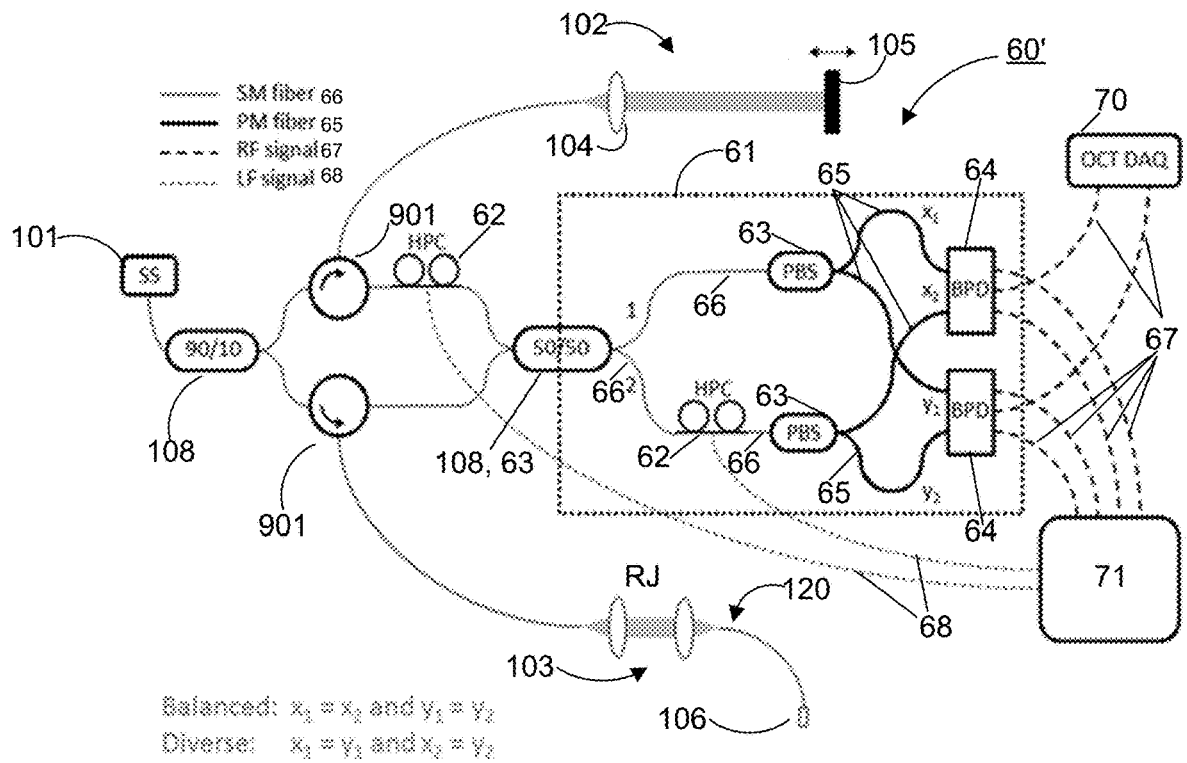
FIG. 7 is at least another embodiment example utilizing automated polarization control, balanced detection and/or polarization diversity in accordance with one or more aspects of the present disclosure.

As shown in FIG. 7, one of the HPCs 62 may be moved outside of the optical controller 60' (which may be the same or similar to the optical controller 60 of FIG. 6, with the exception that the one HPC 62 of the HPCs 62 has been moved outside of the optical controller 60') such that the HPC 62 is located between the circulator 901 of the reference arm 102 and the optical receiver 60', and one of the HPCs 62 remains between the 50/50 splitter (e.g., a deflecting or deflected section 108, a 50/50 PBS 63, etc.) and the bottom PBS 63 of the optical receiver 60'.

Figure 8:
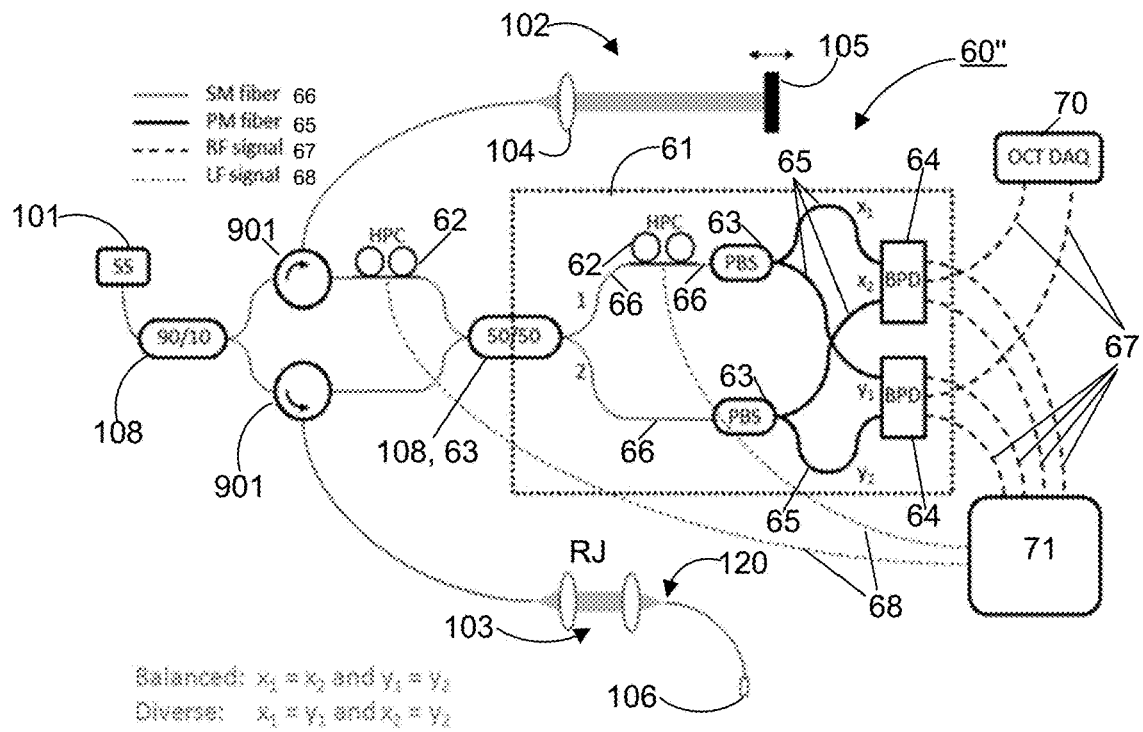
FIG. 8 is at least one embodiment example utilizing automated polarization control, balanced detection and/or polarization diversity in accordance with one or more aspects of the present disclosure.

As shown in FIG. 8, one of the HPCs 62 may be moved outside of the optical controller 60'' (which may be the same or similar to the optical controller 60 of FIG. 6, with the exception that the one HPC 62 of the HPCs 62 has been moved outside of the optical controller 60'') such that the HPC 62 is located between the circulator 901 of the reference arm 102 and the optical receiver 60'', and one of the HPCs 62 remains between the 50/50 splitter (e.g., a deflecting or deflected section 108, a 50/50 PBS 63, etc.) and the top PBS 63 of the optical receiver 60''.

Figure 9:
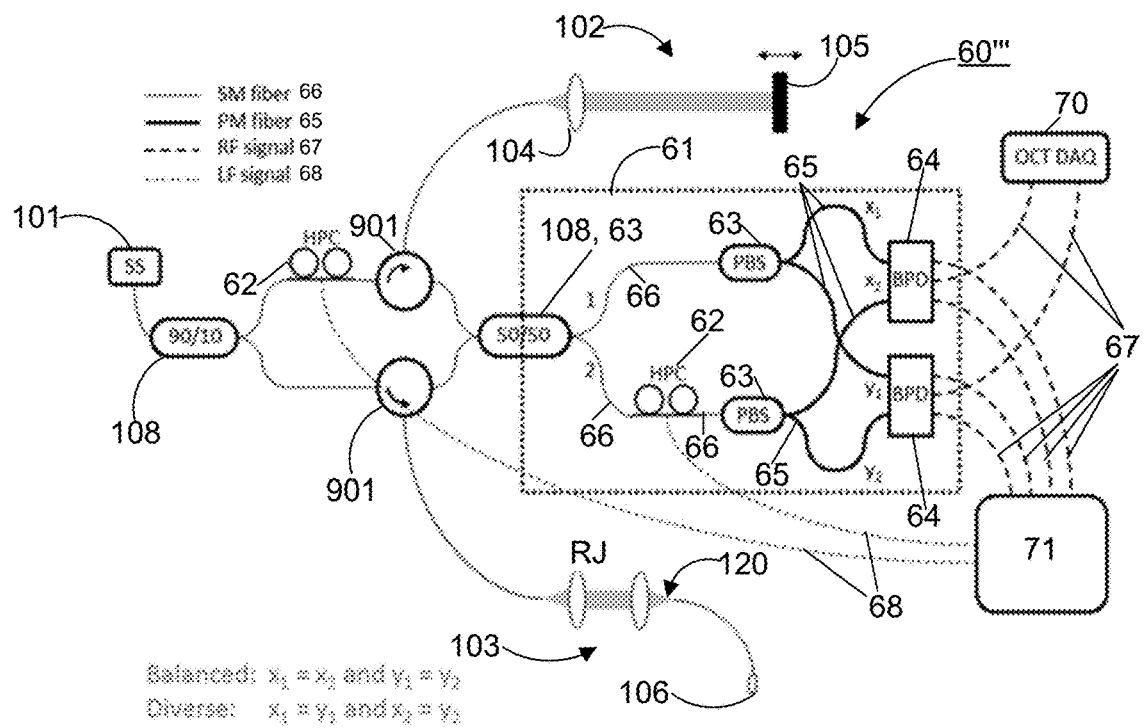
FIG. 9 is at least one embodiment example utilizing automated polarization control, balanced detection and/or polarization diversity in accordance with one or more aspects of the present disclosure.

As shown in FIG. 9, one of the HPCs 62 may be moved outside of the optical controller 60''' (which may be the same or similar to the optical controller 60 of FIG. 6, with the exception that the one HPC 62 of the HPCs 62 has been moved outside of the optical controller 60''') such that the HPC 62 is located between the light source 101 and the circulator 901 of the reference arm 102 (or before the circulator 901 of the reference arm 102), and one of the HPCs 62 remains between the 50/50 splitter (e.g., a deflecting or deflected section 108, a 50/50 PBS 63, etc.) and the bottom PBS 63 of the optical receiver 60'''.

Figure 10:
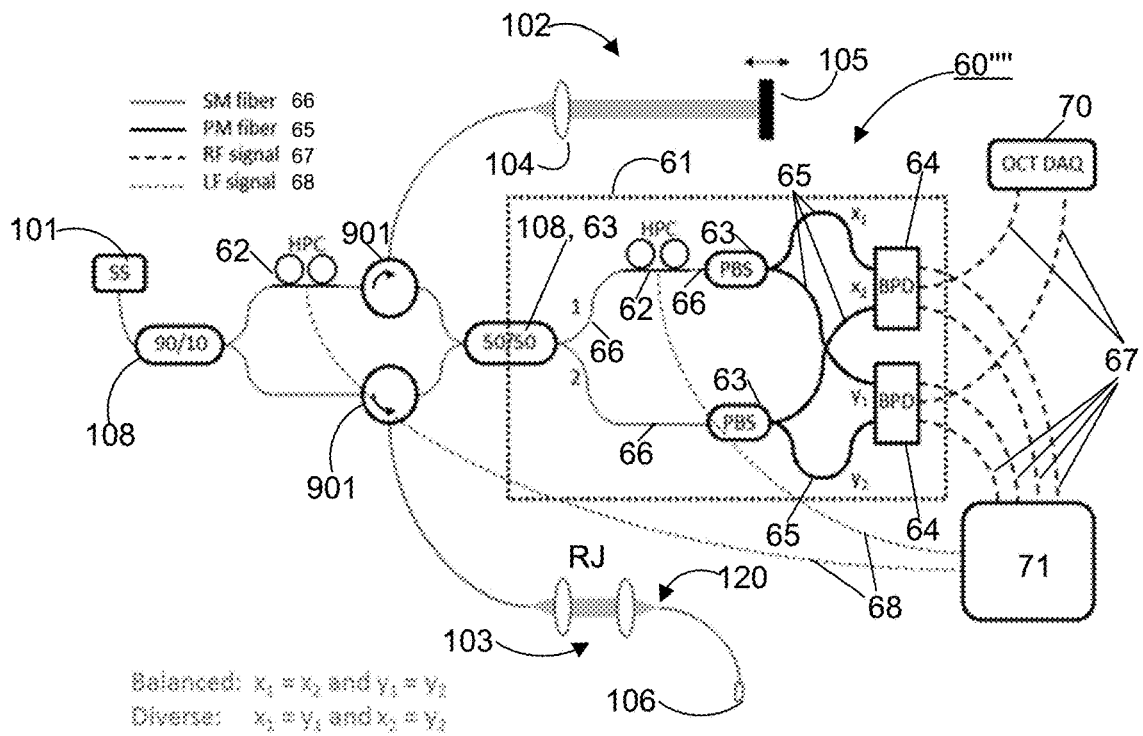
FIG. 10 is at least one embodiment example utilizing automated polarization control, balanced detection and/or polarization diversity in accordance with one or more aspects of the present disclosure.

As shown in FIG. 10, one of the HPCs 62 may be moved outside of the optical controller 60'''' (which may be the same or similar to the optical controller 60 of FIG. 6, with the exception that the one HPC 62 of the HPCs 62 has been moved outside of the optical controller 60'''') such that the HPC 62 is located between the light source 101 and the circulator 901 of the reference arm 102 (or before the circulator 901 of the reference arm 102), and one of the HPCs 62 remains between the 50/50 splitter (e.g., a deflecting or deflected section 108, a 50/50 PBS 63, etc.) and the top PBS 63 of the optical receiver 60''''.

Figure 11:
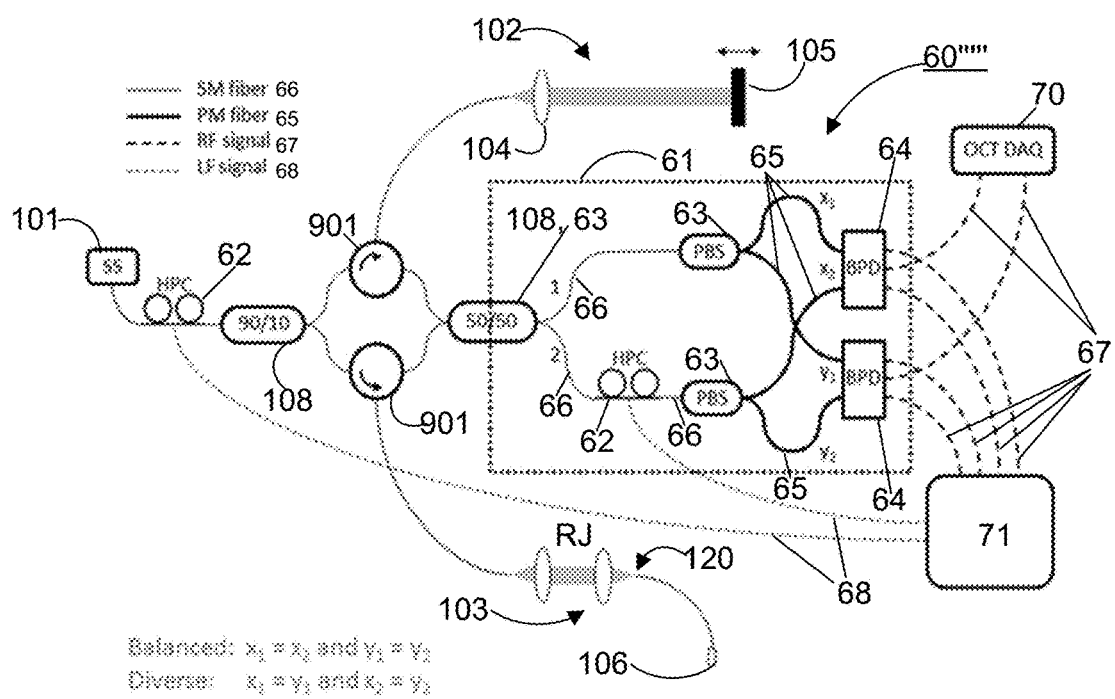
FIG. 11 is at least another embodiment example utilizing automated polarization control, balanced detection and/or polarization diversity in accordance with one or more aspects of the present disclosure.

As shown in FIG. 11, one of the HPCs 62 may be moved outside of the optical controller 60''''' (which may be the same or similar to the optical controller 60 of FIG. 6, with the exception that the one HPC 62 of the HPCs 62 has been moved outside of the optical controller 60''''') such that the HPC 62 is located between the light source 101 and the light splitter 108 (e.g., which splits the light between the two circulators 901, the 90/10 splitter 108, etc.) (or before both of the circulators 901), and one of the HPCs 62 remains between the 50/50 splitter (e.g., a deflecting or deflected section 108, a 50/50 PBS 63, etc.) and the bottom PBS 63 of the optical receiver 60'''''.

Figure 12:
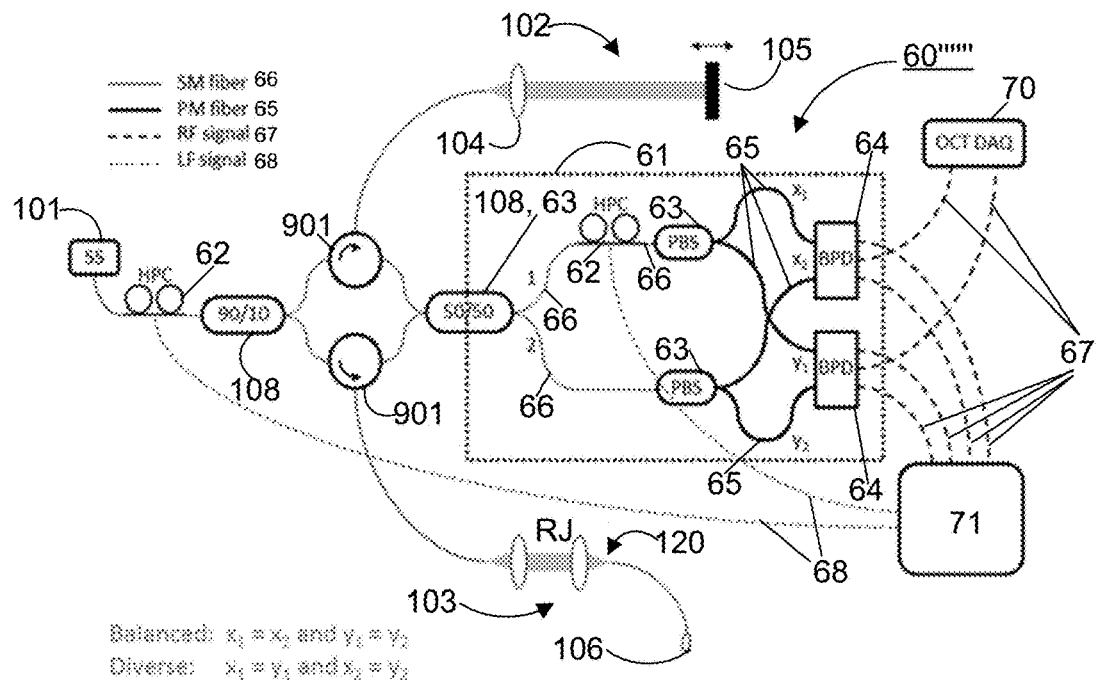
FIG. 12 is at least another embodiment example utilizing automated polarization control, balanced detection and/or polarization diversity in accordance with one or more aspects of the present disclosure.

As shown in FIG. 12, one of the HPCs 62 may be moved outside of the optical controller 60'''''' (which may be the same or similar to the optical controller 60 of FIG. 6, with the exception that the one HPC 62 of the HPCs 62 has been moved outside of the optical controller 60'''''') such that the HPC 62 is located between the light source 101 and the light splitter (e.g., which splits the light between the two circulators 901, the 90/10 splitter 108, etc.) (or before both of the circulators 901), and one of the HPCs 62 remains between the 50/50 splitter (e.g., a deflecting or deflected section 108, a 50/50 PBS 63, etc.) and the top PBS 63 of the optical receiver 60''''''.

One or more hybrid polarization controllers may be motorized. For example, FIG. 5A diagrammatically shows at least one embodiment example of a motorized hybrid polarization controller 62 that may be used in one or more imaging devices, systems or methods (e.g., an embodiment example of an HPC 62). While a different number of paddles may be used as desired as aforementioned, the embodiment of FIG. 5A diagrammatically shows the paddle-type polarization controller 62 being made of two (2) paddles, one motorized (for example, the right paddle in FIG. 5A may be motorized, the left paddle in FIG. 5A may be motorized, etc.) and the other one manually controlled (the left paddle in FIG. 5A in a case where the right paddle is motorized, the right paddle in FIG. 5A in a case where the left paddle is motorized, etc.), hence the term hybrid as aforementioned. HPCs 62 of the present disclosure provide an efficient combination of performance, simplicity, versatility and maintenance considerations. In one or more situations, the manual paddle may be used for initial setup, and the motorized paddle may be used to fine tune the polarization. As discussed above, including for at least FIGS. 6-12, there are numerous ways to control polarization. While the subject example uses paddle-type polarization controllers 62 (or 62', for example), other polarization controller technology may be used additionally or alternatively to the paddle-type structure. While this embodiment employs polarization controllers with two (2) paddles for reasons presented here, alternative embodiments may have less, e.g., one (1) paddle, or more, e.g., three (3) paddles (see e.g., polarization controller 62' of FIG. 5B). Additionally or alternatively, the positions of the manual and motorized paddles may be changed as aforementioned (e.g., the motorized paddle is on the left and the manual paddle is on the right). While this embodiment uses a manual control paddle as aforementioned, other embodiments may employ a fully motorized design (e.g., where the two or more paddles are motorized for full automation). In one or more embodiments, there may be a manual polarization paddle separated from an automated polarization paddle (e.g., the paddles may be integral or connected in one embodiment, the paddles may be separated in another embodiment, etc.). In one or more embodiments, the HPC(s) 62 (or 62') may have two or three motorized paddles per controller with or without manual paddle(s).

From the above equations and features of the present disclosure emerges at least one notion that a device, apparatus, or system (e.g., one or more optical controllers 60, 60', 60", 60''', 60'''', 60''''', 60''''''; device or system 100; device or system 100'; device or system 100"; any other device, system or apparatus discussed herein; etc.) may be optimized by decreasing or minimizing the following quantity equation (1):

$$\text{Polarization error} = \text{abs}(x_1-x_2)+\text{abs}(x_1-y_1)+\text{abs}(x_2-y_2)+\text{abs}(y_1-y_2).$$

In one or more embodiments, an apparatus or system (e.g., one or more optical controllers 60, 60', 60", 60''', 60'''', 60''''', 60''''''; device or system 100; device or system 100'; device or system 100"; any other device, system or apparatus discussed herein; etc.) may be optimized by decreasing or minimizing the following quantity equation (2):

$$\text{Polarization error} = (x_1+\text{ofst}-x_2)+(x_1+\text{ofst}-y_1)+(x_2+\text{ofst}-y_2)+(y_1+\text{ofst}-y_2)-(4*\text{ofst}),$$

where ofst is a predetermined offset value.

Figure 14:
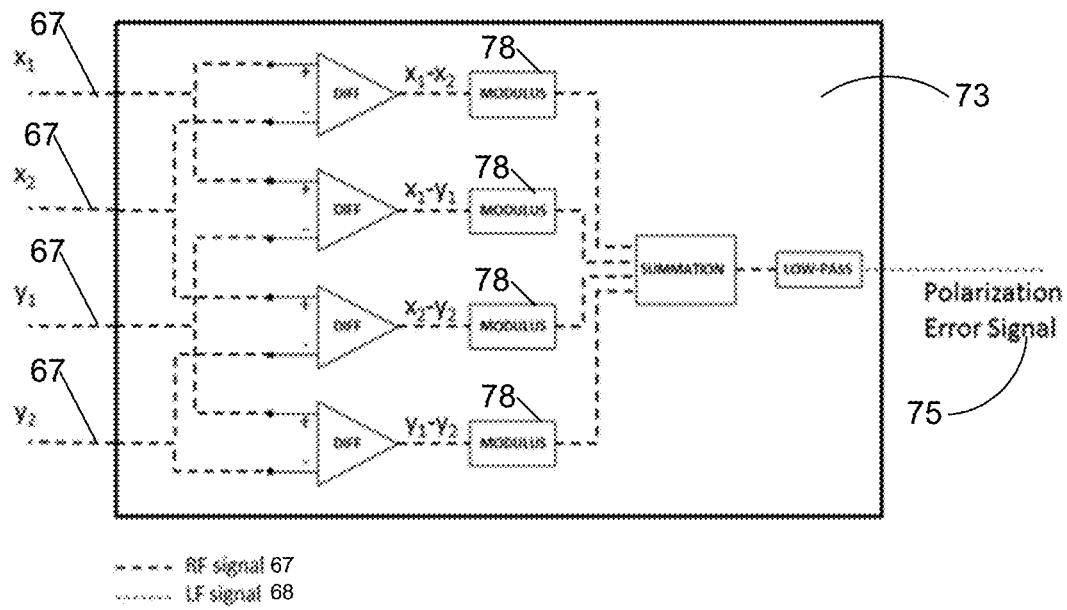
FIG. 14 shows a schematic diagram of at least one embodiment of a polarization control unit signal processing electronic module for handling a polarization error signal in accordance with one or more aspects of the present disclosure.

Using the offset polarization error equation allows one or more embodiments to achieve functionality without using a modulus 78 or rectification block as shown in FIG. 14 as discussed below. In one or more embodiments, the ofst or predetermined offset value may be equal to a maximum signal value x1, x2, y1, or y2 that may be reachable by x1, x2, y1, or y2 such that the respective value(s) in each of the parentheses may be positive and may be performed electronically (e.g., without rectification, without using a modulus 78, without correction since the absolute value may not be used, etc.).

Figure 13:
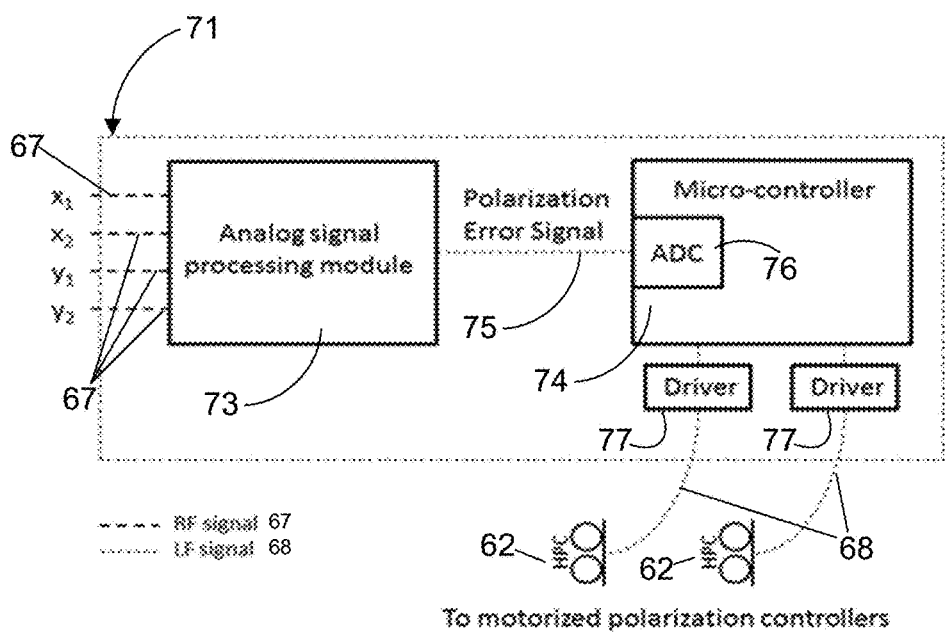
FIG. 13 shows a schematic diagram of at least one embodiment of a polarization control unit (PCU) in accordance with one or more aspects of the present disclosure.

FIGS. 5A-5B, 6-12, and/or FIGS. 13-14 show at least one embodiment of how the polarization error optimization may be achieved. As shown in FIG. 13, the PCU 71 may be made of 2 sub-components (e.g., a first electronic module 73 and at least one micro-controller 74). The first electronic module 73 (which may be an analog signal processing module in one or more embodiments) preferably treats or handles the electrical signals (x1, x2, y1, y2) (e.g., arriving via the RF signal(s) 67). The output of the first electronic module 73 is the polarization error optimization quantity obtained from the equation above, i.e., the polarization error signal 75, which is sent to and sampled by the at least one micro-controller 74 (see e.g., an embodiment example of the first electric module 73 shown in FIG. 13; an embodiment example of the first electronic module 73 shown in FIG. 14; etc.). Using the polarization error signal 75, the at least one micro-controller 74 operates to act upon and drive the motorized polarization controllers (or HPCs, such as the HPCs 62 as shown, for example, in FIGS. 5A-12). Preferably, when the first electronic module 73 handles an analog signal, the at least one micro-controller 74 may include an Analog-to-Digital Converter (ADC) 76. In one or more embodiments, the PCU 71 includes the ADC 76 somewhere outside of the at least one micro-controller 74. In one or more embodiments, the error signal may be generated digitally. For example, the signals representing $x_1$, $y_1$, $x_2$, and $y_2$ may be converted to digital signals via an ADC (e.g., the ADC 76), and the equation(s) for error signal generation may be performed on the digital waveforms and correlated with motor position. As another example, one or more embodiments, may forego inclusion of any analog circuitry (e.g., summing amplifiers, etc.) and instead may use a digitizer with four (4) channels and some kind of processor or computer (e.g., a processor or computer 1200, a processor or computer 1200', a digital version of PCU 71, etc.) that operates to carry out the operations on the digitized waveforms that may be used to produce or generate the error value(s). Using one or more of such configuration(s), a type of control loop may be achieved where the optimal positions of the two HPCs 62 (or 62', for example) may be determined to minimize the polarization error quantity. The micro-controller 74 may be attached to two drivers 77, one for each of the two HPCs 62 (or 62', for example), as shown in FIG. 13. In one or more embodiments, other types of polarization controllers (in addition to or alternatively to paddle type controllers) may be used, such as, but not limited to, a squeezing portion, a rotation portion, a combination of the squeezing portion and the rotation portion, and/or other types of controllers known to those skilled in the art. For example, a squeezing portion and/or a rotation or rotatable portion may be used as provided or sold by Thorlabs (see e.g., Thorlabs polarization controllers as sold/advertised at the following address: https://www.thorlabs.com/newgrouppage9.cfm?objectgroup_ID=2161). In one or more embodiments, a motorized paddle controller, a manual paddle controller, an inline polarization controller, a controller having a squeezing portion, a controller having a rotation or rotatable portion, a controller with any combination of one or more of the above types of controller(s), or any other polarization controller known to those skilled in the art may be used.

The polarization error signal 75 may also be used for manual setup where the error signal 75 is displayed to a monitor and the manual portions of the HPCs 62 (or 62', for example) are adjusted in one or more embodiments. Manual adjustment is typically done for initial setup and also serves as a backup to the automated procedure. That said, manual adjustment may be used after the initial setup as desired.

Further displayed in FIG. 13 is a high-level schematics of the electronic module 73 processing the four (4) raw monitor electric signals (x1, x2, y1, y2). The subject signals may be electronically substrated, amplified, rectified, summed up and filtered electronically according to one or more equations or formula discussed herein (see, for example, the embodiment of FIG. 14). As aforementioned, various polarization error equations may be used, such as, but not limited to, equation (1) above that uses the modulus 78/rectification block of the PCU 71 signal processing shown in FIG. 14, equation (2) above that may be used with or without modulus 78/rectification block of the PCU 71 signal processing of FIG. 14, etc. The subject signals may also be a radio-frequency (RF) signal in one or more embodiments. The output of the first processing module 73 may be a low frequency (LF) signal.

An additional feature that may be used is to low-pass filter the final polarization error signal (as shown, for example, in FIG. 14). Implementing a low-pass filter enables an embodiment to forgo any sort of synchronization to acquire the error signal at the micro-controller level. The low-pass filter may be adjusted so that its cutoff frequency is around 1 kHz. The end result is a signal filtered out of all higher frequencies but changing quickly enough to any mechanical adjustment of the polarization controllers 71.

As aforementioned, the second part of the PCU 71 is the at least one micro-controller 74. The at least one micro-controller 74 (and/or firmware thereof) may operate to one or more of the following: sample the polarization error signal 75, control the two (2) (or other number of) motorized polarization controllers 62 (or 62', for example), and manage a control loop to reduce or minimize the polarization error.

While at least one micro-controller 74 is used in the embodiment examples of FIGS. 13-14 to perform the control operations, one or more embodiments of the present disclosure are not limited to using the at least one micro-controller 74 to perform the control operations. In one or more embodiments, such control is not limited to a specific type of hardware, and the same or similar results may certainly be achieved using other structure, such as, but not limited to, Digital Signal Processing (DSP), Field Programmable Gate Array(s) (FPGA), etc. Within micro-controllers 74, a large selection also exists (e.g., 8 bit, 16 bit, 32 bit, etc.), and the hardware may be selected by a user of the device, apparatus, or system (e.g., one or more optical controllers 60, 60', 60", 60''', 60'''', 60''''', 60''''''; device or system 100; device or system 100'; device or system 100"; any other device, system, or apparatus discussed herein; etc.) based on the desired specifications and/or the desired applications.

Figure 15:
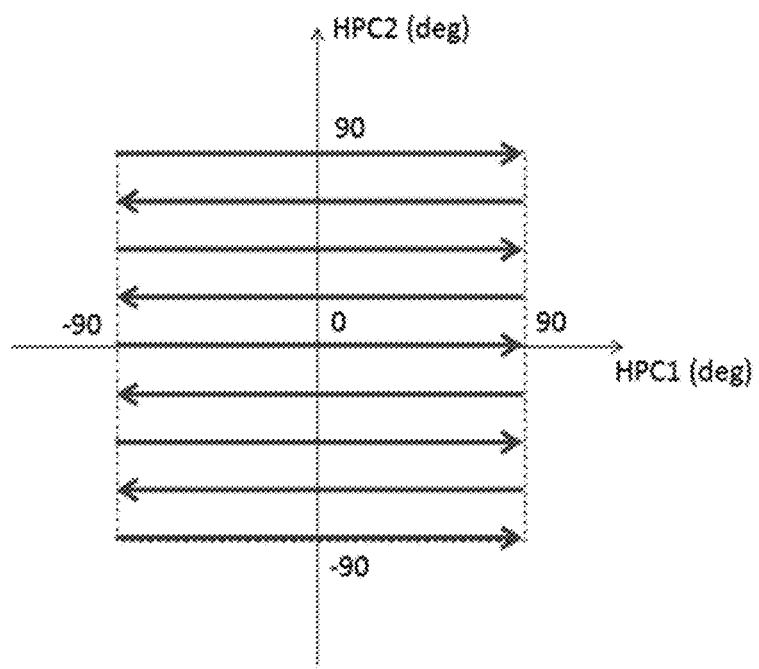
FIG. 15 is at least one embodiment of a raster scan approach that may be used in one or more embodiments discussed herein to determine positions of or for at least two polarization controllers to reduce or minimize a polarization error signal in accordance with one or more aspects of the present disclosure.

FIG. 15 shows at least one embodiment approach or method for finding the positions of the two (2) polarization controllers 62 (e.g., the two HPCs 62 (or 62', for example)) where the polarization control error signal 75 (also referred to herein as a "polarization error signal") is greatly reduced or at a minimum. Preferably, the two positions are found where the error signal 75 is minimized. Specifically, at least one embodiment may raster scan the entire range of possibilities for the positions of the two polarization controllers 62 (or 62', for example). One or more alternative embodiments may employ other approaches, and may be desirable to find the positions of the greatly reduced or minimum error signal. In other words, the polarization controller 62 (or 62', for example) position determination features of the present disclosure are not limited to the raster scan approach.

One or more embodiments of the present disclosure refine the raster scan approach as best as possible where granularity of the scan may be adjusted. By way of at least one example, the scan granularity on FIG. 15 is made extremely wide (e.g., 22.5 deg) for illustration purposes. It is understood that a much finer granularity may be required in one or more embodiments and that the option to change granularity or to scan a given region of interest (ROI) provides some benefits. Ultimately, the goal is to find the greatly reduced or minimum error accurately in the least amount of time (such as, but not limited to, <30 seconds). On FIG. 15, the scan is made of individual sweeps where at least one polarization controller 62 (or 62', for example) moves across its adjustment range (e.g., rotation of the polarization controller 62 (or 62', for example) paddle may be made over an angular range of 180 deg) while the other polarization controller 62 (or 62', for example) remains still. Such a sweep, along with error signal 75 acquisition, may be executed by the micro-controller 74, as shown in FIG. 16.

Figure 16:
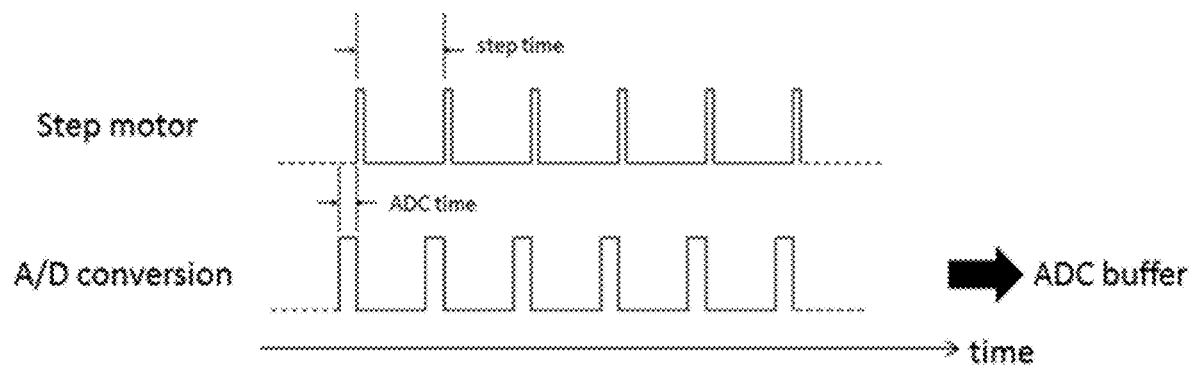
FIG. 16 shows at least one embodiment of an execution of a sweep over time in accordance with one or more aspects of the present disclosure.

In one or more embodiments, for example as shown in FIG. 16, the micro-controller 74 may command the stepper motor (or step motor) driving the polarization controller 62 (or 62', for example) to advance one step by pulsing a step-and-direction driver (see e.g., the driver(s) 77 discussed above). The error signal may be sampled prior to stepping to the next position. This way, the micro-controller 74 is able to measure the error signal 75 as a function of the position of the polarization controller 62 (or 62', for example).

Figure 17:
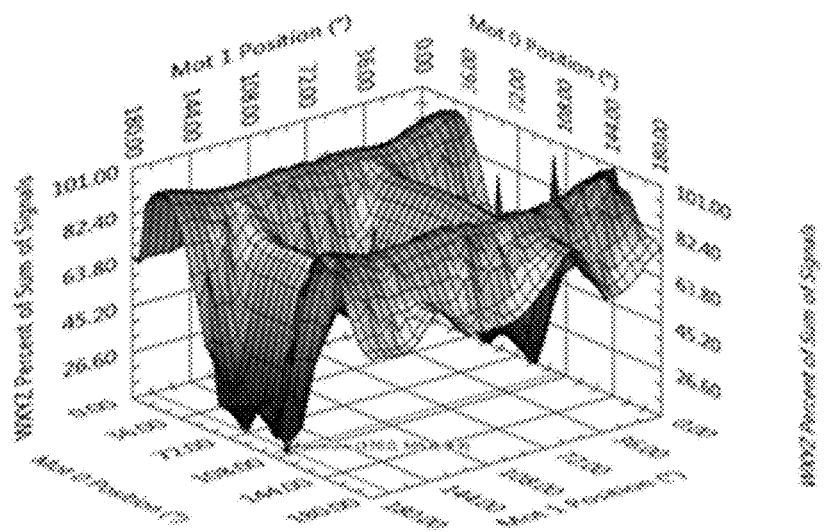
FIG. 17 shows at least one embodiment of results and an evolution of a polarization error as a function of positions of polarization controllers in accordance with one or more aspects of the present disclosure.

FIG. 17 shows at least one embodiment example of an actual result showing an evolution of the polarization error as a function of the positions of the polarization controllers 62 (or 62', for example). The information in FIG. 17 provide an idea of the optimization range that is available. FIG. 17 also shows intricate, detailed, or complex peaks and valleys as well as very rapid changes. In one or more embodiments, the intricate, detailed, or complex nature of the peaks and valleys, as well as the very rapid changes, illustrates the need and usefulness of controlling polarization as discussed herein.

Figure 18A:
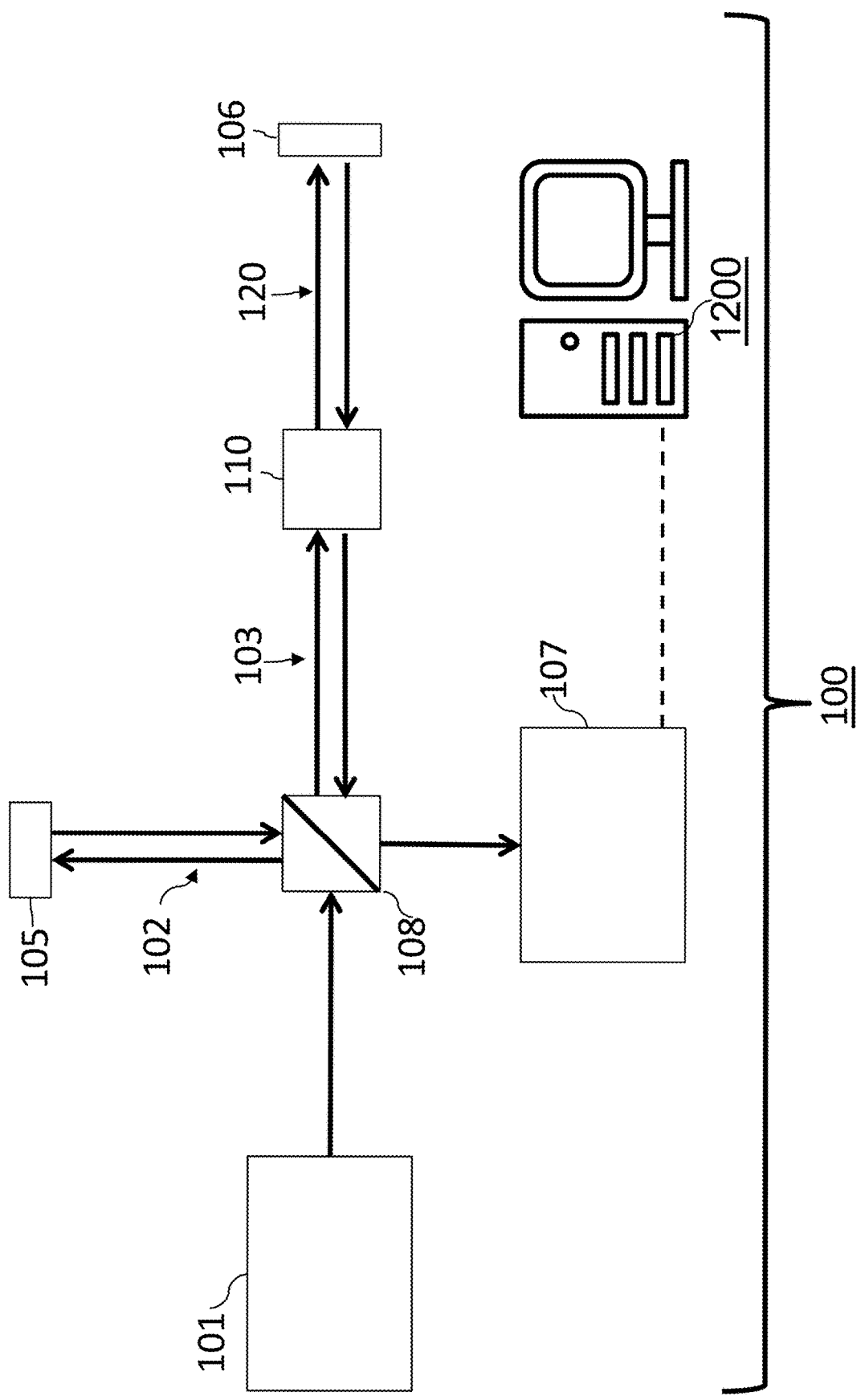
FIG. 18A shows at least one embodiment of an OCT apparatus or system for utilizing automated polarization control, balanced detection and/or polarization diversity in accordance with one or more aspects of the present disclosure.

FIG. 18A shows an OCT system 100 (as referred to herein as "system 100" or "the system 100") which may be used to achieve one or more of automated polarization control, polarization diversity, and/or balanced detection in accordance with one or more aspects of the present disclosure. The system 100 comprises a light source 101, a reference arm 102, a sample arm 103, a deflected or deflecting section 108, a reference mirror (also referred to as a "reference reflection", "reference reflector", "partially reflecting mirror" and a "partial reflector") 105, and one or more detectors 107 (which may be connected to a computer 1200). In one or more embodiments, the system 100 may include a patient interface device or unit ("PIU") 110 and a catheter 120 (see e.g., embodiment examples of a catheter 120 as shown in FIGS. 6-12), and the system 100 may interact with a sample, object, patient (e.g., a blood vessel of a patient), target 106 (e.g., via the catheter 120 and/or the PIU 110). In one or more embodiments, the system 100 includes an interferometer or an interferometer is defined by one or more components of the system 100, such as, but not limited to, at least the light source 101, the reference arm 102, the sample arm 103, the deflecting section 108 and the reference mirror 105.

Figure 18B:
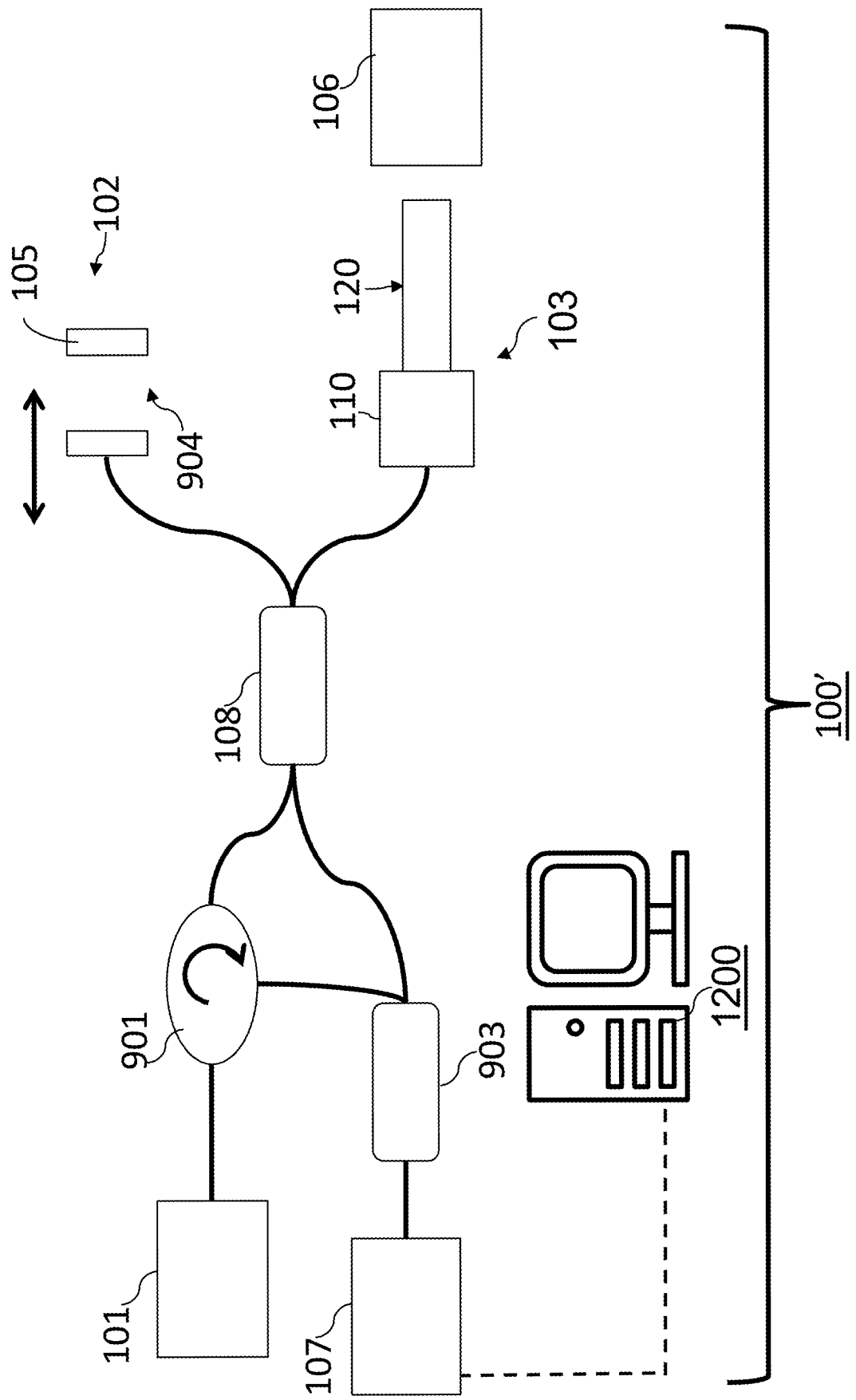
FIG. 18B shows at least another embodiment of an OCT apparatus or system for using automated polarization control, balanced detection and/or polarization diversity in accordance with one or more aspects of the present disclosure.

In accordance with one or more further aspects of the present disclosure, bench top systems may be utilized with the automated polarization control, polarization diversity, and/or balanced detection technique(s) (and/or feature(s) or function(s)/option(s)) and/or selecting an appropriate automated polarization control, polarization diversity, and/or balanced detection method as disclosed herein. FIG. 18B shows an example of a system that can utilize the automated polarization control, polarization diversity, and/or balanced detection technique(s) (and/or feature(s) or function(s)/option(s)) and/or selecting an appropriate automated polarization control, polarization diversity, and/or balanced detection method for a bench-top such as for ophthalmic applications. A light from a light source 101 delivers and splits into a reference arm 102 and a sample arm 103 with a deflecting section 108. A reference beam goes through a length adjustment section 904 and is reflected from a reference mirror (such as or similar to the reference mirror or reference reflection 105 shown in FIG. 18A) in the reference arm 102 while a sample beam is reflected or scattered from a sample, target, object, patient (e.g., blood vessel of a patient), etc. 106 in the sample arm 103 (e.g., via the PIU 110 and the catheter 120). In one embodiment, both beams combine at the deflecting section 108 and generate interference patterns. In one or more embodiments, the beams go to the combiner 903, and the combiner 903 combines both beams via the circulator 901 and the deflecting section 108, and the combined beams are delivered to one or more detectors (such as the one or more detectors 107). The output of the interferometer is continuously acquired with one or more detectors, such as the one or more detectors 107. The electrical analog signals are converted to the digital signals to analyze them with a computer, such as, but not limited to, the computer 1200 (see FIGS. 18A-18C; also shown in FIG. 20 discussed further below), the computer 1200' (see e.g., FIG. 21 discussed further below), etc. Additionally or alternatively, one or more of the polarization control units 71, optical receivers (e.g., 60, 60', 60", 60''', 60'''', 60''''', 60'''''', any other optical receiver discussed herein, etc.) and/or controllers 74 may be used to process the electrical signals as discussed above or may be used along with or part of the computer 1200, the computer 1200', any other processor discussed herein, etc.

Figure 18C:
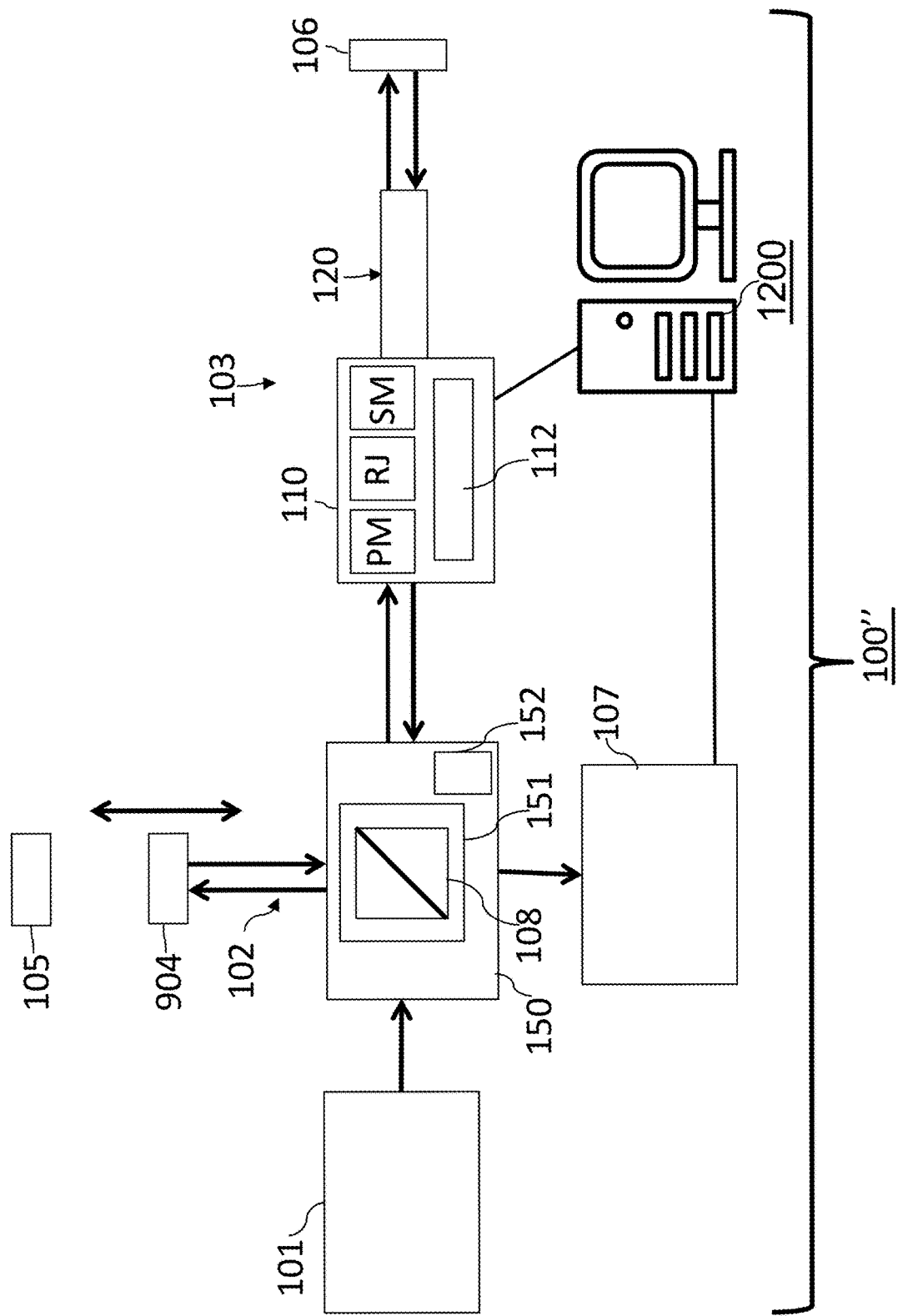
FIG. 18C shows at least a further embodiment of an OCT apparatus or system for using automated polarization control, balanced detection and/or polarization diversity in accordance with one or more aspects of the present disclosure.

In accordance with one or more further aspects of the present disclosure, one or more other systems may be utilized with the automated polarization control, polarization diversity, and/or balanced detection technique(s) (and/or feature(s) or function(s)/option(s)) and/or selecting an appropriate automated polarization control, polarization diversity, and/or balanced detection method as disclosed herein. FIG. 18C shows an example of a system 100" that may utilize the automated polarization control, polarization diversity, and/or balanced detection technique(s) (and/or feature(s) or function(s)/option(s)) and/or selecting an appropriate automated polarization control, polarization diversity, and/or balanced detection method such as for ophthalmic applications. A light from a light source 101 delivers and splits into a reference arm 102 and a sample arm 103 with a deflecting section 108 (e.g., a beamsplitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may go or pass through a length adjustment section 904, which may operate to change the distance of a reference mirror (such as reference mirror or reference reflection 105; also shown in FIG. 18A for example) and is reflected from the reference reflection 105 in the reference arm 102 while a sample beam is reflected or scattered from a sample, target, object, patient (e.g., blood vessel of a patient), etc. 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see FIGS. 18A-18C; also shown in FIG. 20 discussed further below), the computer 1200' (see e.g., FIG. 21 discussed further below), etc. Additionally or alternatively, one or more of the polarization control units 71, optical receivers (e.g., 60, 60', 60", 60''', 60'''', 60''''', 60'''''', any other optical receiver discussed herein, etc.), and/or controllers (e.g., controller 74) may be used to process the electrical signals as discussed above, or may be used with or as part of a computer, such as, but not limited to, the computer 1200, the computer 1200', any other computer or processor discussed herein, etc. In one or more embodiments, the sample arm 103 includes the PIU 11o and the catheter 120 so that the sample beam is reflected or scattered from the sample, target, object, patient (e.g., blood vessel of a patient), etc. 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIG. 18C; see also, the rotary junction RJ in FIGS. 6-12). The rotary junction RJ may be connected to the spin motor SM so that the catheter 120 may obtain one or more views or images of the sample, target, object, patient (e.g., blood vessel of a patient), etc. 106. The computer 1200 (or the computer 1200') may be used to control one or more of the pullback motor PM, the spin motor SM, and/or the motion control unit 112. An OCT system may include one or more of the OCT engine 150, a computer (e.g., the computer 1200, the computer 1200', etc.), the PIU 11o, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Preferably, in one or more embodiments including the deflecting or deflected section 108 (best seen in FIGS. 18A-18C), the deflected section 108 operates to deflect the light from the light source 101 to the reference arm 102 and/or the sample arm 103, and then send light received from the reference arm 102 and/or the sample arm 103 towards the at least one detector 107 (e.g., a spectrometer, one or more components of the spectrometer, another type of detector, etc.). In one or more embodiments, the deflected section (e.g., the deflected section 108 of the system 100, 100', 100", any other system discussed herein, etc.) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 (or any other system discussed herein) such as, but not limited to, one or more of the light source 101, the deflected section 108, the rotary junction RJ, a PIU 110, a catheter 120, etc. One or more features of the aforementioned configurations of at least FIGS. 6-17 may be incorporated into one or more of the systems, including, but not limited to, the system 100, 100', 100'', any other system, etc. discussed herein.

While not limited to such arrangements, configurations, devices or systems, one or more embodiments of the methods discussed herein may be used with an apparatus or system as aforementioned, such as, but not limited to, for example, the system 100, the system 100', the system 100'', the devices, apparatuses, or systems of FIGS. 6-17, any other device, apparatus, or system discussed herein, etc. In one or more embodiments, one user may perform the method(s) discussed herein. In one or more embodiments, one or more users may perform the method(s) discussed herein.

The light source 101 may include a plurality of light sources or may be a single light source. The light source 101 may be a broadband lightsource, and may include one or more of a laser, an organic light emitting diode (OLED), a light emitting diode (LED), a halogen lamp, an incandescent lamp, supercontinuum light source pumped by a laser, and/or a fluorescent lamp. The light source 101 may be any light source that provides light which may then be dispersed to provide light which is then used for imaging, performing automated polarization control, performing balanced detection and achieving polarization diversity, selecting an appropriate automated polarization control, balanced detection, and polarization diversity method, and/or any other method discussed herein. The light source 101 may be fiber coupled or may be free space coupled to the other components of the apparatus and/or system 100, 100', 100'', the devices, apparatuses or systems of FIGS. 6-17, or any other embodiment discussed herein. As aforementioned, the light source 101 may be a swept-source (SS) light source.

Additionally or alternatively, the one or more detectors 107 may be a linear array, a charge-coupled device (CCD), a plurality of photodiodes or some other method of converting the light into an electrical signal. The detector(s) 107 may include an analog to digital converter (ADC). The one or more detectors may be detectors having structure as shown in one or more of FIGS. 6-17 and as discussed above.

Figure 19:
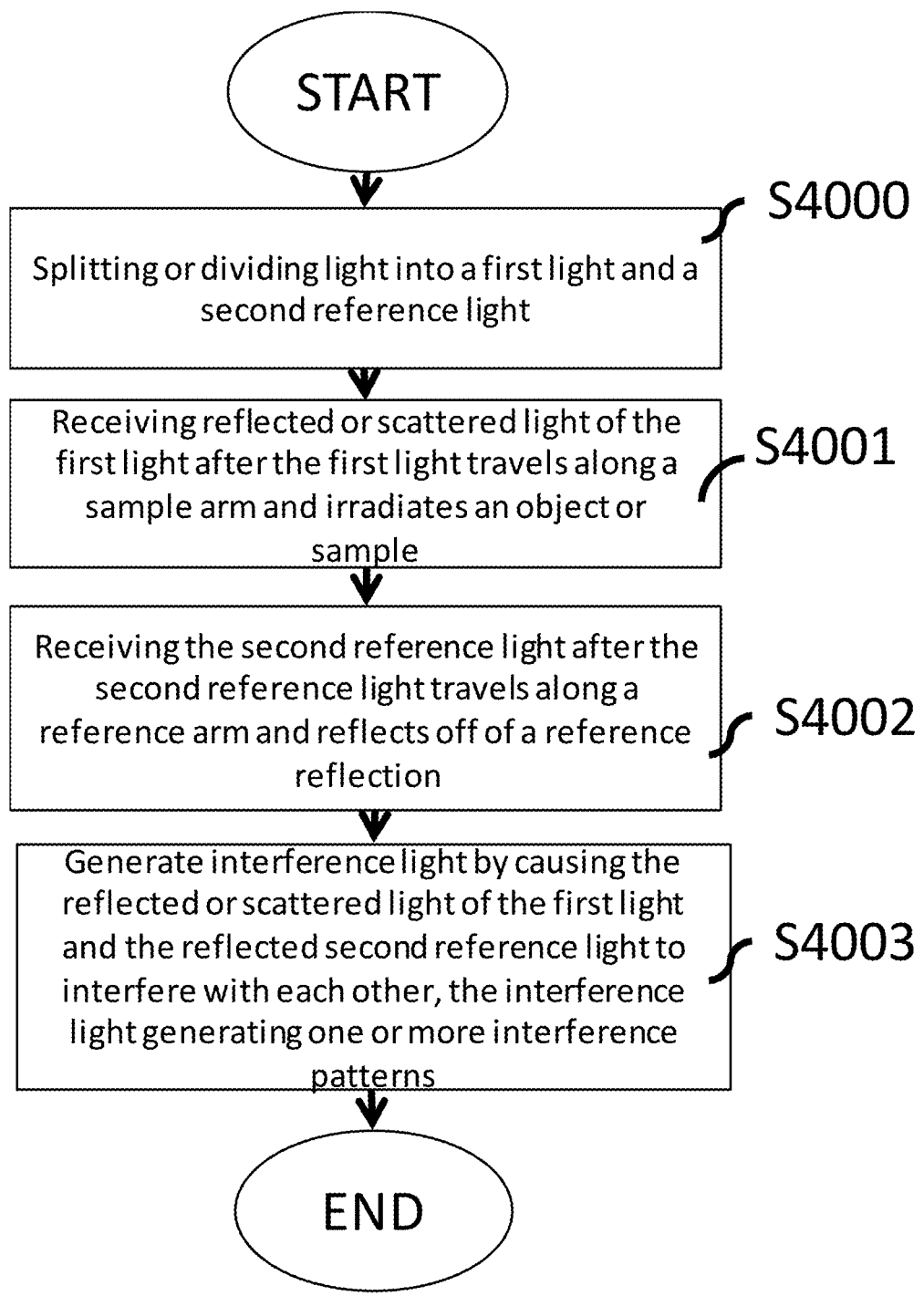
FIG. 19 is a flow diagram showing a method of performing an imaging feature, function or technique in accordance with one or more aspects of the present disclosure.

In accordance with one or more aspects of the present disclosure, one or more methods for performing imaging are provided herein. FIG. 19 illustrates a flow chart of at least one embodiment of a method for performing imaging. Preferably, the method(s) may include one or more of the following: (i) splitting or dividing light into a first light and a second reference light (see step S4000 in FIG. 19); (ii) receiving reflected or scattered light of the first light after the first light travels along a sample arm and irradiates an object or a sample (see step S4001 in FIG. 19); (iii) receiving the second reference light after the second reference light travels along a reference arm and reflects off of a reference reflection (see step S4002 in FIG. 19); and generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 19). One or more methods may further include using low frequency monitors to update or control high frequency content to improve image quality. For example, one or more embodiments may use balanced detection, polarization diversity, automated polarization control, etc. to achieve improved image quality. In one or more embodiments, an imaging probe may be connected to one or more systems (e.g., the system 100, the system 100', the system 100'', the devices, apparatuses or systems of FIGS. 6-17, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

The one or more detectors 107 may transmit the digital or analog signals to a processor or a computer such as, but not limited to, an image processor, a processor or computer 1200, 1200' (see e.g., FIGS. 18A-18C and 20-21), a combination thereof, etc. The image processor may be a dedicated image processor or a general purpose processor that is configured to process images. In at least one embodiment, the computer 1200, 1200' may be used in place of, or in addition to, the image processor. In an alternative embodiment, the image processor may include an ADC and receive analog signals from the one or more detectors 107. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the devices, apparatuses, or systems of FIGS. 5A-17, the computer 1200, the computer 1200', the image processor, may also include one or more components further discussed herein below (see e.g., FIGS. 20-21). In one or more embodiments, the aforementioned PCU 71 may be used as part of or in addition to the subject computer or processor.

In at least one embodiment, a console or computer 1200, 1200' operates to control motions of the RJ via the motion control unit (MCU) 112 or a motor M, acquires intensity data from the detector(s) in the one or more detectors 107, and displays the scanned image (e.g., on a monitor or screen such as a display, screen or monitor 1209 as shown in the console or computer 1200 of any of FIGS. 18A-18C and FIG. 20 and/or the console 1200' of FIG. 21 as further discussed below). In one or more embodiments, the MCU 112 or the motor M operates to change a speed of a motor of the RJ and/or of the RJ. The motor may be a stepping or a DC servomotor to control the speed and increase position accuracy.

The output of the one or more components of any of the systems discussed herein may be acquired with the at least one detector 107, e.g., such as, but not limited to, photodiodes, Photomultiplier tube(s) (PMTs), line scan camera(s), or multi-array camera(s). Electrical analog signals obtained from the output of the system 100, 100', 100", and/or the detector(s) 107 thereof, and/or from the devices, apparatuses, or systems of FIGS. 5A-17, are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Unless otherwise discussed herein, like numerals indicate like elements. For example, while variations or differences exist between the systems, such as, but not limited to, the system 100, the system 100', the system 100", or any other device, apparatus or system discussed herein, one or more features thereof may be the same or similar to each other, such as, but not limited to, the light source 101 or other component(s) thereof (e.g., the console 1200, the console 1200', etc.). Those skilled in the art will appreciate that the light source 101, the motor or MCU 112, the RJ, the at least one detector 107, and/or one or more other elements of the system 100 may operate in the same or similar fashion to those like-numbered elements of one or more other systems, such as, but not limited to, the devices, apparatuses or systems of FIGS. 5A-17, the system 100', the system 100", or any other system discussed herein. Those skilled in the art will appreciate that alternative embodiments of the devices, apparatuses or systems of FIGS. 5A-17, the system 100', the system 100", any other device, apparatus or system discussed herein, etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100 of FIG. 18A and one or more embodiments shown in any of FIGS. 5A-18C, for example, as discussed herein, there are similarities. Likewise, while the console or computer 1200 may be used in one or more systems (e.g., the system 100, the system 100', the system 100", the devices, apparatuses, or systems of any of FIGS. 5A-17, or any other system discussed herein, etc.), one or more other consoles or computers, such as the console or computer 1200', may be used additionally or alternatively.

There are many ways to compute intensity, viscosity, resolution (including increasing resolution of one or more images), automated polarization control, balanced detection, and polarization diversity, selecting an appropriate automated polarization control, performing balanced detection, and achieving polarization diversity method or any other measurement discussed herein, digital as well as analog. In at least one embodiment, a computer, such as the console or computer 1200, 1200', may be dedicated to control and monitor the imaging (e.g., OCT, single mode OCT, multimodal OCT, etc.) devices, systems, methods and/or storage mediums described herein.

The electric signals used for imaging may be sent to one or more processors, such as, but not limited to, a computer 1200 (see e.g., FIGS. 18A-18C and 20), a computer 1200' (see e.g., FIG. 21), etc. as discussed further below, via cable(s) or wire(s), such as, but not limited to, the cable(s) or wire(s) 113 (see FIG. 20). Additionally or alternatively, the electric signals, as aforementioned, may be processed in one or more embodiments as discussed above by the PCU 71 or components thereof.

Figure 20:
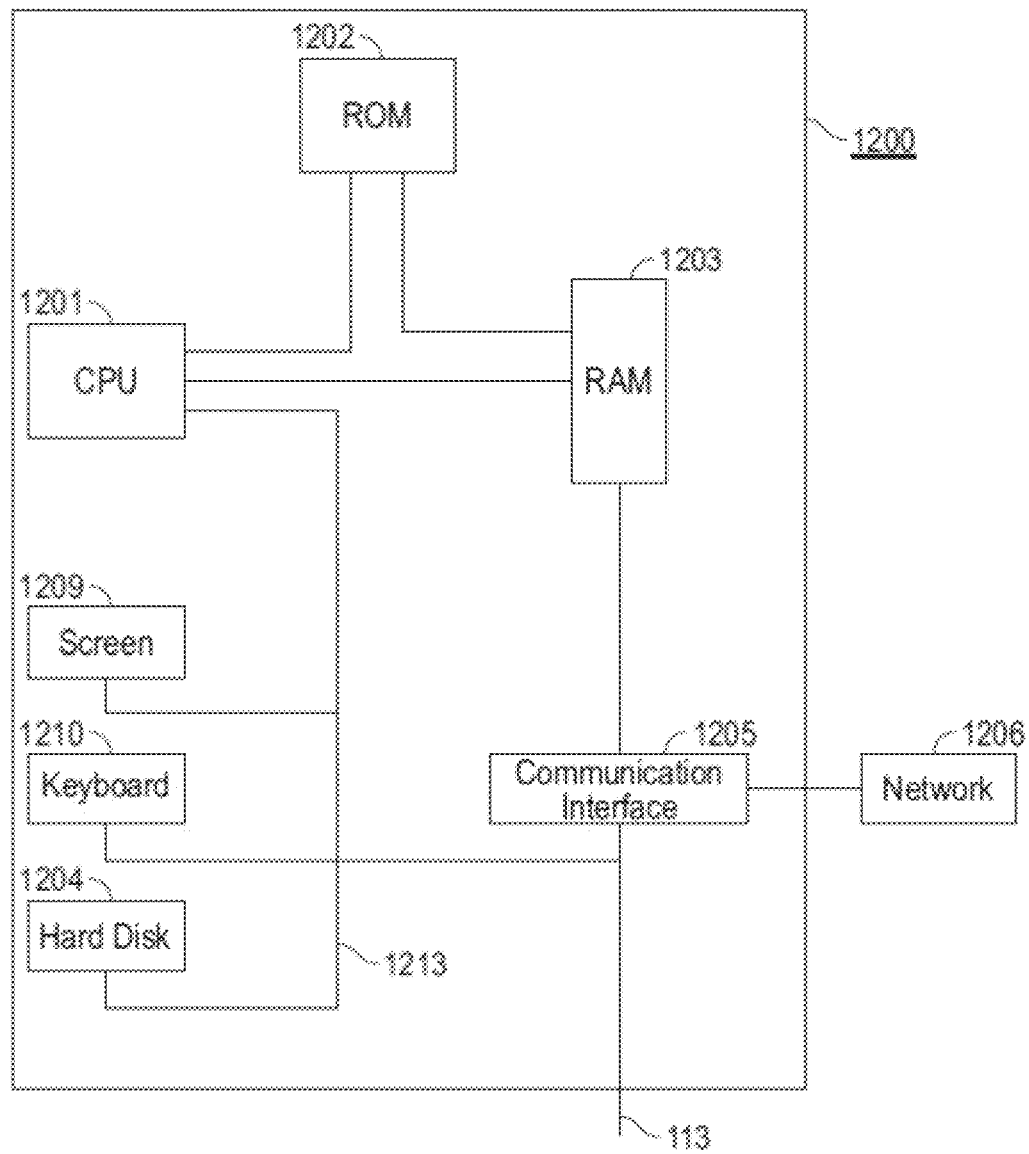
FIG. 20 shows a schematic diagram of an embodiment of a computer that may be used with one or more embodiments of an imaging apparatus or system one or more methods discussed herein in accordance with one or more aspects of the present disclosure.

Various components of a computer system 1200 are provided in FIG. 20. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., including but not limited to, being connected to the console, the probe, the imaging apparatus or system, any motor discussed herein, a light source, etc.). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a device or system, such as, but not limited to, an apparatus or system using one or more automated polarization control, polarization diversity, and/or balanced detection technique(s) (and/or feature(s) or function(s)/option(s)) and/or selecting an appropriate automated polarization control, polarization diversity, and/or balanced detection method(s) as discussed herein), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for tissue or sample characterization, diagnosis, evaluation and/or imaging. The system 1200 may further include one or more processors connected via a network connection (e.g., via network 1206). The CPU 1201 and any additional processor being used by the system 1200 may be located in the same telecom network or in different telecom networks (e.g., performing feature(s), function(s), technique(s), method(s), etc. discussed herein may be controlled remotely). Additionally or alternatively, the PCU 71 may be used as part of or outside of any of the processors or computers discussed herein.

Figure 21:
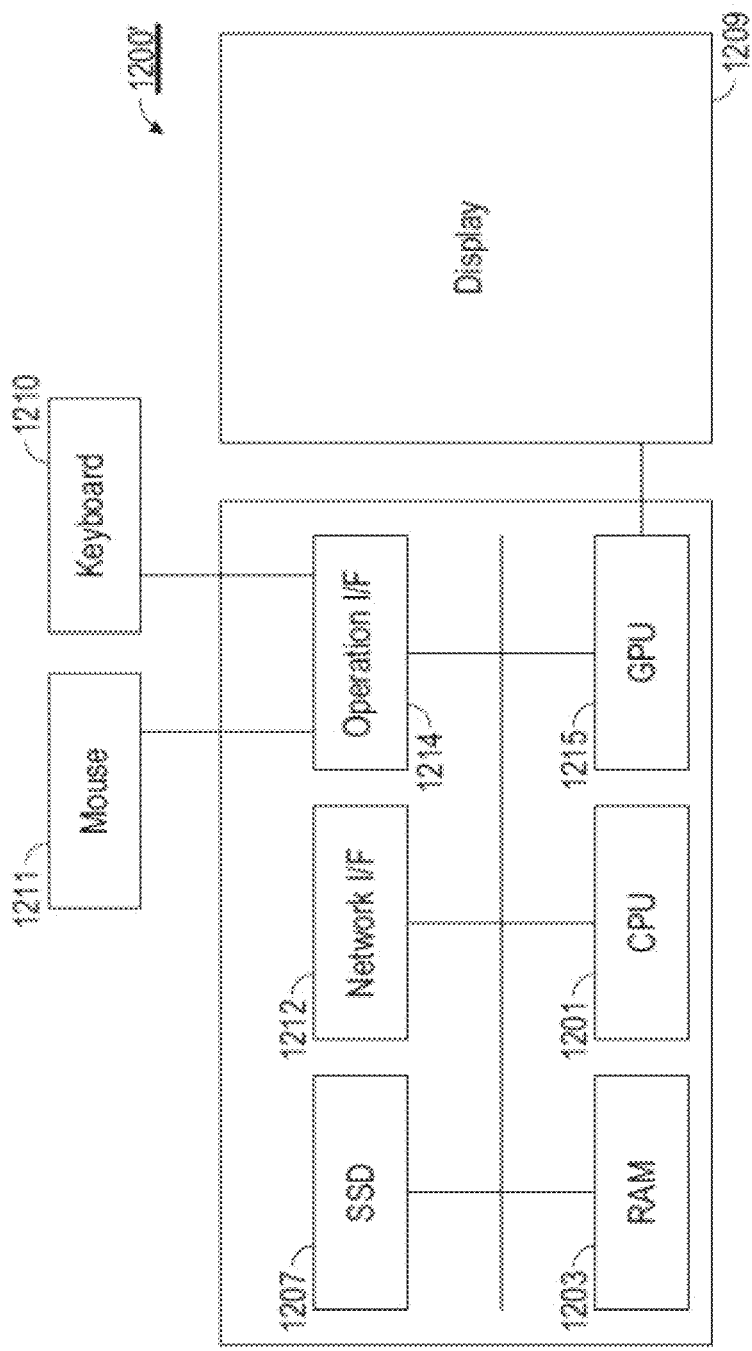
FIG. 21 shows a schematic diagram of another embodiment of a computer that may be used with one or more embodiments of an imaging apparatus or system or methods discussed herein in accordance with one or more aspects of the present disclosure.

The I/O or communication interface 1205 provides communication interfaces to input and output devices, which may include a light source, a spectrometer, the communication interface of the computer 1200 may connect to other components discussed herein via line 113 (as diagrammatically shown in FIG. 20), a microphone, a communication cable and a network (either wired or wireless), a keyboard 1210, a mouse (see e.g., the mouse 1211 as shown in FIG. 21), a touch screen or screen 1209, a light pen and so on. The Monitor interface or screen 1209 provides communication interfaces thereto.

Any methods and/or data of the present disclosure, such as the methods for performing tissue or sample characterization, diagnosis, examination and/or imaging (including, but not limited to, increasing image resolution, performing automated polarization control, polarization diversity, and/or balanced detection, selecting an appropriate automated polarization control, polarization diversity, and/or balanced detection method (and/or option(s) or feature(s)), etc.), for example, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 21), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 20. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 20) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium. The computers or processors (e.g., 1200, 1200', etc.) may include the aforementioned PCU 71, or may be connected to the PCU 71 for communication therewith.

As aforementioned, hardware structure of an alternative embodiment of a computer or console 1200' is shown in FIG. 21. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with a motor, a console, or any other component of the device(s) or system(s) discussed herein via the operation interface 1214 or the network interface 1212 (e.g., via a cable or fiber, such as the cable or fiber 113 as similarly shown in FIG. 20). A computer, such as the computer 1200', may include a motor or motion control unit (MCU) in one or more embodiments. The operation interface 1214 is connected with an operation unit such as a mouse device 1211, a keyboard 1210 or a touch panel device. The computer 1200' may include two or more of each component.

At least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

The computer, such as the computer 1200, 1200', (or other component(s) such as, but not limited to, the PCU 71, the HPC(s) 62 (or 62', for example), etc.) may communicate with an MCU, an interferometer, a spectrometer, a detector, etc. to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate any system discussed herein. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs any system discussed herein to set or change the imaging condition (e.g., improving resolution of an image or images), and to start or end the imaging. A light or laser source and a spectrometer and/or detector may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/0101374, and 2016/0228097, and WO 2016/144878, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. An optical coherence tomography (OCT) system for performing automated polarization control, performing balanced detection and achieving polarization diversity, the system comprising:
    an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and to interfere, with each other, the interference light generating one or more interference patterns;
    at least a first detector and a second detector that operate to continuously acquire the interference light and/or the one or more interference patterns to measure the interference or the one or more interference patterns between the combined or recombined light;
    at least one polarization control processor (PCP) that operates to perform automated polarization control, perform balanced detection, and achieve polarization diversity;
    an optical receiver that operates to receive the combined or recombined interference light and split the light into two signals based on a predetermined ratio or a 50/50 ratio, wherein the two split signals go through polarization controls and wherein the optical receiver further splits the two signals each into two signals for a total of four signals; and
    at least one processor that operates to perform OCT data acquisition for imaging,
    wherein the first detector is in communication with the optical receiver such that the first detector receives two of the four signals of the optical receiver and outputs a first signal, a second signal, and a third signal, where the first and second signals of the first detector are transmitted to the at least one polarization control processor, and the second detector is in communication with the optical receiver such that the second detector receives the other two of the four signals of the optical receiver and outputs a fourth signal, a fifth signal, and a sixth signal, where the fourth and fifth signals of the second detector are transmitted to the at least one polarization control processor,
    wherein the third signal from the first detector and the sixth signal from the second detector are transmitted to the at least one processor for performing OCT data acquisition for imaging, and
    wherein the at least one polarization control processor further operates to receive the first, second, fourth, and fifth signals and use the first, second, fourth, and fifth signals to generate a polarization error signal and/or at least one additional signal, the polarization error signal and/or the at least one additional signal being used by the at least one polarization control processor to perform the automated polarization control, perform the balanced detection, and/or achieve the polarization diversity.

2. The system of claim 1, further comprising at least one polarization controller that communicates with the at least one polarization control processor, via the at least one additional signal of the at least one polarization control processor, to perform the automated polarization control, perform the balanced detection, and achieve the polarization diversity.

3. The system of claim 2,
    wherein the at least one polarization controller includes at least one hybrid polarization controller having a manually controlled portion and an automated portion and that operates to achieve the automated polarization control.

4. The system of claim 3, wherein one or more of the following:
    (i) the at least one hybrid polarization controller comprises two hybrid polarization controllers, and at least a first of the two hybrid polarization controllers is disposed or located in the optical receiver while at least a second of the two hybrid polarization controllers is disposed or located in one of the following locations: in the optical receiver, in or along the reference arm before the light arrives at the optical receiver, or in between the light source and the reference arm;
    (ii) the at least one hybrid polarization controller comprises two hybrid polarization controllers, and the two hybrid polarization controllers are connected to the PCP such that the PCP controls the two hybrid polarization controllers; and/or
    (iii) the at least one additional signal of the at least one polarization control processor comprises two additional signals and the at least one hybrid polarization controller comprises two hybrid polarization controllers, where a first of the two hybrid polarization controllers is connected to the PCP via a first signal of the two additional signals and a second of the two hybrid polarization controllers is connected to the PCP via a second signal of the two additional signals.

5. The system of claim 3, wherein one or more of the following:
(i) the optical receiver further comprises two paths, a first path for the first of the two signals of the optical receiver and a second path for the second of the two signals of the optical receiver;
(ii) each of two paths, the two paths comprising a first path for the first of the two signals of the optical receiver and a second path for the second of the two signals of the optical receiver, includes and/or is connected to at least one polarizing beam splitter and at least one of the first and second detectors, the first and second detectors each being a balanced detector or balanced photo-detector;
(iii) a first of at least two polarizing beam splitters operates to split the first signal of the optical receiver into two of the four signals of the optical receiver that are equal to, or substantially equal to, each other, and a second of the at least two polarizing beam splitters operates to split the second signal of the optical receiver into two other signals of the four signals of the optical receiver that are equal to, or substantially equal to, each other such that the optical receiver achieves the balanced detection;
(iv) the four signals of the optical receiver are all equal to, or substantially equal to, each other such that the optical receiver achieves the polarization diversity;
(v) the first and second detectors, which are balanced detectors or balanced photo-detectors, are connected to the at least one polarization control processor such that the PCP uses the first, second, fourth, and fifth signals as raw monitor outputs from the first and second balanced detectors or balanced photo-detectors to control the at least one hybrid polarization controller;
(vi) the first and second detectors, which are balanced detectors or balanced photo-detectors, are connected to the at least one processor that operates to perform OCT data acquisition for imaging, the at least one processor that performs OCT data acquisition being attached to or including an OCT data acquisition board (DAQ) that operates to collect OCT data and/or main balanced output from the first and second balanced detectors or balanced photo-detectors; and/or
(vii) the optical receiver includes the first and second detectors.

6. The system of claim 5, wherein the PCP includes:
(i) a first electric signal or analog signal processing module that operates to receive and process the first, second, fourth, and fifth signals of the first and second detectors to determine a reduced or minimized polarization control error signal and to output the polarization control error signal, or a digital signal or a digitizer having four channels that operates to receive and process the first, second, fourth, and fifth signals of the first and second detectors to determine the reduced or minimized polarization control error signal and to output the polarization control error signal; and
(ii) at least one controller or micro-controller that operates to receive or sample the output polarization control error signal and to one or more of: (a) control the automated portion of the at least one hybrid polarization controller and (b) manage a control loop to minimize, or maintain the reduction or minimization of, the polarization control error signal.

7. The system of claim 6, wherein, in a case where the PCP includes a first electric signal or analog signal processing module, one or more of the following:
(i) the output of the first electric signal or analog signal processing module is low-pass filtered before the at least one controller or micro-controller receives or samples the output polarization control error signal; and/or
(ii) the at least one controller or micro-controller includes an Analog-to-Digital converter to convert and process the output polarization control error signal to drive the automated portion of the at least one hybrid polarization controller.

8. The system of claim 1, wherein the second reference light includes 90%, or about 90%, of a laser intensity from the light source, and the first light includes 10%, or about 10%, of the laser intensity from the light source, or
wherein the first light includes 90%, or about 90%, of a laser intensity from the light source, and the second reference light includes 10%, or about 10%, of the laser intensity from the light source.

9. The system of claim 1, further comprising a first circulator and a second circulator, the first circulator operating to pass the first light from the light source to the sample arm, and to pass the reflected or scattered light of the first light to or towards the at least one detector, and the second circulator operating to pass the second reference light from the light source to the reference arm and to pass the reflected second reference light from the reference arm to or towards the at least one detector.

10. A method for controlling an optical coherence tomography (OCT) device or system having an interference optical system that operates to generate interference light and one or more interference patterns from a light that has been split into a first light with which an object or sample has been irradiated and a second reference light, having a first detector and a second detector, having at least one polarization control processor (PCP) that operates to perform automated polarization control, perform balanced detection and achieve polarization diversity, having an optical receiver that operates to receive the combined or recombined interference light and split the light into two signals based on a predetermined ratio or a 50/50 ratio, wherein the two split signals go through polarization controls and wherein the optical receiver further splits the two signals each into two signals for a total of four signals, and at least one processor that operates to perform OCT data acquisition for imaging, the method comprising:
transmitting two of the four signals of the optical receiver to the first detector such that the first detector outputs a first signal, a second signal, and a third signal, where the first and second signals of the first detector are transmitted to the at least one polarization control processor, and transmitting the other two of the four signals of the optical receiver to the second detector such that the second detector outputs a fourth signal, a fifth signal, and a sixth signal, where the fourth and fifth signals of the second detector are transmitted to the at least one polarization control processor,
transmitting the third signal from the first detector and the sixth signal from the second detector to the at least one processor for performing OCT data acquisition for imaging, and
transmitting the first, second, fourth, and fifth signals to the at least one polarization control processor such that the at least one polarization control processor uses the first, second, fourth, and fifth signals to generate a polarization error signal and/or at least one additional signal, the polarization error signal and/or the at least one additional signal being used by the at least one polarization control processor to perform automated or motorized polarization control, balanced detection, and polarization diversity such that the OCT device or system has increased or optimized signal-to-noise ratio and improved image quality.

11. The method of claim 10, wherein the OCT device or system further comprises at least one polarization controller that communicates, via the at least one additional signal of the at least one polarization control processor, with the at least one polarization control processor to perform the automated polarization control, perform the balanced detection, and achieve the polarization diversity.

12. The method of claim 11,
wherein the at least one polarization controller includes at least one hybrid polarization controller having a manually controlled portion and an automated portion and that operates to achieve the automated polarization control.

13. The method of claim 12, further comprising one or more of the following:
(i) disposing or locating at least a first of the at least one hybrid polarization controller in the optical receiver;
(ii) disposing or locating at least a second of the at least one hybrid polarization controller in one of the following locations: in the optical receiver, in or along a reference arm of the OCT device or system before the light arrives at the optical receiver, or in between a light source of the OCT device or system and the reference arm;
(iii) controlling first and second hybrid polarization controllers of the at least one hybrid polarization controller with the PCP; and/or
(iv) controlling first and second hybrid polarization controllers of the at least one hybrid polarization controller with the PCP, where the at least one additional signal of the at least one polarization control processor comprises two additional signals, where the first of the two hybrid polarization controllers is connected to the PCP via a first signal of the two additional signals and the second of the two hybrid polarization controllers is connected to the PCP via a second signal of the two additional signals.

14. The method of claim 12, wherein one or more of the following:
(i) the optical receiver further comprises two paths, a first path for the first of the two signals of the optical receiver and a second path for the second of the two signals of the optical receiver;
(ii) each of two paths, the two paths comprising a first path for the first of the two signals of the optical receiver and a second path for the second of the two signals of the optical receiver, includes and/or is connected to at least one polarizing beam splitter and at least one of the first and second detectors, the first and second detectors each being a balanced detector or balanced photo-detector;
(iii) a first of at least two polarizing beam splitters operates to split the first signal of the optical receiver into two of the four signals of the optical receiver that are equal to, or substantially equal to, each other, and a second of the at least two polarizing beam splitters operates to split the second signal of the optical receiver into two other signals of the four signals of the optical receiver that are equal to, or substantially equal to, each other such that the optical receiver achieves the balanced detection;
(iv) the four signals of the optical receiver are all equal to, or substantially equal to, each other such that the optical receiver achieves the polarization diversity;
(v) the first and second detectors, which are balanced detectors or balanced photo-detectors, are connected to the at least one polarization control processor such that the PCP uses the first, second, fourth, and fifth signals as raw monitor outputs from the first and second balanced detectors or balanced photo-detectors to control the at least one hybrid polarization controller;
(vi) the first and second detectors, which are balanced detectors or balanced photo-detectors, are connected to the at least one processor that operates to perform OCT data acquisition for imaging, the at least one processor that performs OCT data acquisition being attached to or including an OCT data acquisition board (DAQ) that operates to collect OCT data and/or main balanced output from the first and second balanced detectors or balanced photo-detectors; and/or
(vii) the optical receiver includes the first and second detectors.

15. The method of claim 14, wherein the PCP includes:
(i) a first electric signal or analog signal processing module that operates to receive and process the first, second, fourth, and fifth signals of the first and second detectors to determine a reduced or minimized polarization control error signal and to output the polarization control error signal, or a digital signal or a digitizer having four channels that operates to receive and process the first, second, fourth, and fifth signals of the first and second detectors to determine the reduced or minimized polarization control error signal and to output the polarization control error signal; and
(ii) at least one controller or micro-controller that operates to receive or sample the output polarization control error signal and to one or more of: (a) control the automated portion of the at least one hybrid polarization controller and (b) manage a control loop to minimize, or maintain the reduction or minimization of, the polarization control error signal.

16. The method of claim 15, further comprising, in a case where the PCP includes a first electric signal or analog signal processing module, one or more of the following:
(i) low-pass filtering the output of the first electric signal or analog signal processing module before the at least one controller or micro-controller receives or samples the output polarization control error signal; and/or
(ii) converting, via an Analog-to-Digital converter of the at least one controller or micro-controller, and processing the output polarization control error signal to drive the automated portion of the at least one hybrid polarization controller.

17. The method of claim 10, further comprising dividing the first light and the second reference light from a light source of the OCT device or system, wherein the second reference light includes 90%, or about 90%, of a laser intensity from the light source, and the first light includes 10%, or about 10%, of the laser intensity from the light source, or
wherein the first light includes 90%, or about 90%, of a laser intensity from the light source, and the second reference light includes 10%, or about 10%, of the laser intensity from the light source.

18. The method of claim 10, further comprising:
providing a first circulator and a second circulator in the OCT device or system, the first circulator operating to pass the first light from a light source of the OCT device or system to a sample arm of the OCT device or system and to pass reflected or scattered light of the first light to or towards the at least one detector, and the second circulator operating to pass the second reference light from the light source to a reference arm of the OCT device or system and to pass the reflected second reference light from the reference arm to or towards the at least one detector.

19. The method of claim 10, wherein one or more of the following:
   (i) the polarization diversity and balanced detection are optimized; and/or
   (ii) the first and second detectors are automatically adjusted to maximize the interference light and resulting interference pattern.

20. A non-transitory computer-readable storage medium storing at least one program for causing a computer to execute a method for controlling an optical coherence tomography (OCT) device or system having an interference optical system that operates to generate interference light and one or more interference patterns from a light that has been split into a first light with which an object or sample has been irradiated and a second reference light, and having a first detector and a second detector, having at least one polarization control processor (PCP) that operates to perform automated polarization control, perform balanced detection and achieve polarization diversity, having an optical receiver that operates to receive the combined or recombined interference light and split the light into two signals based on a predetermined ratio or a 50/50 ratio, wherein the two split signals go through polarization controls and wherein the optical receiver further splits the two signals each into two signals for a total of four signals, and at least one processor that operates to perform OCT data acquisition for imaging, the method comprising:
   transmitting two of the four signals of the optical receiver to the first detector such that the first detector outputs a first signal, a second signal, and a third signal, where the first and second signals of the first detector are transmitted to the at least one polarization control processor, and transmitting the other two of the four signals of the optical receiver to the second detector such that the second detector outputs a fourth signal, a fifth signal, and a sixth signal, where the fourth and fifth signals of the second detector are transmitted to the at least one polarization control processor,
   transmitting the third signal from the first detector and the sixth signal from the second detector to the at least one processor for performing OCT data acquisition for imaging, and
   transmitting the first, second, fourth, and fifth signals to the at least one polarization control processor such that the at least one polarization control processor uses the first, second, fourth, and fifth signals to generate a polarization error signal and/or at least one additional signal, the polarization error signal and/or the at least one additional signal being used by the at least one polarization control processor to perform automated or motorized polarization control, balanced detection, and polarization diversity such that the OCT device or system has increased or optimized signal-to-noise ratio and improved image quality.

21. The storage medium of claim 20, wherein one or more of the following:
   (i) the polarization diversity and balanced detection are optimized; and/or
   (ii) the first and second detectors are automatically adjusted to maximize the interference light and resulting interference pattern.

* * * * *